(12) United States Patent
Rozentals et al.

(10) Patent No.: US 12,043,535 B2
(45) Date of Patent: Jul. 23, 2024

(54) PERSONALIZED DIETARY SUPPLEMENT DISPENSING DEVICE

(71) Applicant: H2Yo, Parkland, FL (US)

(72) Inventors: Edgars Rozentals, Riga (LV); Alehandro Georgs Blumentals, Riga (LV); Konstantin Othmer, Los Altos Hills, CA (US)

(73) Assignee: H2YO, Parkland, FL (US)

( * ) Notice: Subject to any disclaimer, the term of this patent is extended or adjusted under 35 U.S.C. 154(b) by 842 days.

(21) Appl. No.: 17/117,670

(22) Filed: Dec. 10, 2020

(65) Prior Publication Data

US 2022/0185646 A1 Jun. 16, 2022

(51) Int. Cl.
*B67D 1/00* (2006.01)
*A61J 7/00* (2006.01)
(Continued)

(52) U.S. Cl.
CPC .......... *B67D 1/0034* (2013.01); *A61J 7/0046* (2013.01); *A61J 7/0084* (2013.01); *A61J 7/0418* (2015.05); *B67D 1/004* (2013.01); *B67D 1/0888* (2013.01); *G05B 15/02* (2013.01); *G06K 7/10297* (2013.01); *G06K 19/0723* (2013.01); *G06Q 10/087* (2013.01); *G06Q 50/06* (2013.01); *G16H 10/60* (2018.01); *G16H 20/13* (2018.01);
(Continued)

(58) Field of Classification Search
CPC .................................................... A61J 7/0418
See application file for complete search history.

(56) References Cited

U.S. PATENT DOCUMENTS

| 1,591,799 A | 7/1926 | Tinapp |
| 3,060,703 A | 10/1962 | Benua et al. |

(Continued)

FOREIGN PATENT DOCUMENTS

| CA | 2124681 C | 6/2003 |
| CN | 101346288 B | 11/2012 |

(Continued)

OTHER PUBLICATIONS

International Search Report and Written Opinion of the ISA dated Mar. 24, 2022 as received in Application No. PCT/US2021/61316.

*Primary Examiner* — Gene O Crawford
*Assistant Examiner* — Ayodeji T Ojofeitimi
(74) *Attorney, Agent, or Firm* — Maschoff Brennan

(57) ABSTRACT

A dispenser can include: an optional water source inlet; a plurality of supplement cartridges including a supplement composition; at least one dispenser fluidly coupled with the optional water source inlet and plurality of supplement cartridges; a formulation mechanism operably coupled with the optional water source inlet and supplement cartridges, wherein the formulation mechanism is configured for regulating fluid flow from the optional water source inlet and the supplement cartridges to the dispenser; an input device configured to receive input from a user; and a dispenser controller. The dispenser controller can be configured to: receive identification information from a user via the input device; obtain a supplement dosage formulation for the user based on a personalized supplement protocol; and control dispensing of water and supplement composition(s) to provide the supplement dosage formulation to the user.

23 Claims, 13 Drawing Sheets

(51) Int. Cl.

| | | |
|---|---|---|
| *A61J 7/04* | (2006.01) | |
| *B67D 1/08* | (2006.01) | |
| *G05B 15/02* | (2006.01) | |
| *G06K 7/10* | (2006.01) | |
| *G06K 19/07* | (2006.01) | |
| *G06Q 10/087* | (2023.01) | |
| *G06Q 50/06* | (2012.01) | |
| *G16H 10/60* | (2018.01) | |
| *G16H 20/13* | (2018.01) | |
| *G16H 20/60* | (2018.01) | |
| *G16H 40/67* | (2018.01) | |
| *G16H 50/70* | (2018.01) | |

(52) U.S. Cl.
CPC ............ *G16H 20/60* (2018.01); *G16H 40/67* (2018.01); *G16H 50/70* (2018.01); *A61J 7/049* (2015.05)

(56) References Cited

U.S. PATENT DOCUMENTS

| | | | |
|---|---|---|---|
| 3,218,175 A | 11/1965 | Siegel et al. | |
| 3,250,433 A | 5/1966 | Christine et al. | |
| 3,363,807 A | 1/1968 | Powell | |
| 3,572,553 A | 3/1971 | Ogden | |
| 3,848,776 A | 11/1974 | Schieser | |
| 3,987,715 A * | 10/1976 | Muller | A47J 31/401 |
| | | | 99/275 |
| 4,015,755 A | 4/1977 | Lerner et al. | |
| 4,030,634 A | 6/1977 | Osborn | |
| 4,595,131 A | 6/1986 | Ruskin et al. | |
| 4,755,292 A | 7/1988 | Merriam | |
| 4,958,747 A | 9/1990 | Sheets | |
| 5,114,047 A | 5/1992 | Baron et al. | |
| 5,256,279 A | 10/1993 | Voznick et al. | |
| 5,312,017 A | 5/1994 | Schroeder et al. | |
| 5,390,826 A | 2/1995 | Burrows | |
| 5,531,908 A | 7/1996 | Matsumoto et al. | |
| 5,540,355 A | 7/1996 | Hancock et al. | |
| 6,073,539 A | 6/2000 | Triola et al. | |
| 6,196,420 B1 | 3/2001 | Gutierrez et al. | |
| 6,223,944 B1 | 5/2001 | Gehl et al. | |
| 6,382,467 B2 | 5/2002 | Saveliev et al. | |
| 6,453,955 B1 | 9/2002 | Lee | |
| 6,557,735 B1 | 5/2003 | Stray | |
| 6,793,099 B1 | 9/2004 | Sleiman | |
| 7,028,603 B1 | 4/2006 | Gremillion et al. | |
| 7,295,889 B2 * | 11/2007 | Lahteenmaki | G16H 20/60 |
| | | | 700/239 |
| 7,438,941 B2 | 10/2008 | Gutwein et al. | |
| 7,669,738 B1 | 3/2010 | Byers | |
| 7,703,382 B2 | 4/2010 | Oranski et al. | |
| 7,762,181 B2 | 7/2010 | Boland et al. | |
| 7,806,294 B2 | 10/2010 | Gapiton et al. | |
| 7,861,646 B2 | 1/2011 | Bockbrader | |
| 7,912,579 B2 * | 3/2011 | Stettes | G07F 13/065 |
| | | | 700/231 |
| 8,170,405 B2 | 5/2012 | Harris | |
| 8,309,030 B2 | 11/2012 | Rinker et al. | |
| 8,606,379 B2 | 12/2013 | Marrushella et al. | |
| 8,728,535 B2 | 5/2014 | Squashic et al. | |
| 8,768,524 B2 | 7/2014 | Hammonds et al. | |
| 9,051,162 B2 | 6/2015 | Peters et al. | |
| 9,212,041 B2 | 12/2015 | Keating et al. | |
| 9,533,867 B2 | 1/2017 | Hortin | |
| 9,622,615 B2 | 4/2017 | Hecht et al. | |
| 9,646,314 B2 | 5/2017 | Moore et al. | |
| 9,668,508 B2 | 6/2017 | Chandra et al. | |
| 9,679,329 B2 | 6/2017 | Jones | |
| 9,773,265 B2 | 9/2017 | Sharpley | |
| 9,790,079 B2 | 10/2017 | Groesbeck | |
| 9,932,217 B2 | 4/2018 | Perrelli et al. | |
| 10,017,372 B2 | 7/2018 | Bethuy et al. | |
| 10,059,581 B2 | 8/2018 | Peters et al. | |
| 10,231,567 B2 | 3/2019 | Perrelli et al. | |
| 10,279,985 B2 | 5/2019 | Mills et al. | |
| 10,435,285 B2 | 10/2019 | Lim et al. | |
| 10,464,797 B2 | 11/2019 | James et al. | |
| 10,674,857 B2 | 6/2020 | Lyons et al. | |
| 10,694,655 B2 | 6/2020 | Wintemute et al. | |
| 10,723,541 B2 | 7/2020 | Akdogan et al. | |
| 10,765,252 B2 | 9/2020 | Perrelli et al. | |
| 2005/0092769 A1 | 5/2005 | Machler et al. | |
| 2006/0000851 A1 | 1/2006 | Girard et al. | |
| 2006/0115570 A1 | 6/2006 | Guerrero et al. | |
| 2006/0118581 A1 | 6/2006 | Clark | |
| 2009/0064866 A1 | 3/2009 | Shultis | |
| 2010/0146587 A1 | 6/2010 | Sholes et al. | |
| 2013/0092567 A1 | 4/2013 | Lok | |
| 2014/0239013 A1 | 8/2014 | Santos | |
| 2015/0105880 A1 | 4/2015 | Slupik | |
| 2016/0058245 A1 | 3/2016 | Smith et al. | |
| 2017/0099981 A1 | 4/2017 | Haidar et al. | |
| 2018/0130141 A1 | 5/2018 | Carpenter et al. | |
| 2019/0084757 A1 | 3/2019 | Brysch et al. | |
| 2019/0233183 A1 | 8/2019 | Linton et al. | |

FOREIGN PATENT DOCUMENTS

| | | |
|---|---|---|
| EP | 2733122 A1 | 5/2014 |
| IE | 47040 | 7/1978 |
| RU | 2487415 C2 | 7/2013 |
| WO | 2001079072 A1 | 10/2001 |
| WO | 2005/111955 A1 | 11/2005 |
| WO | 2020/010322 A1 | 1/2020 |

* cited by examiner

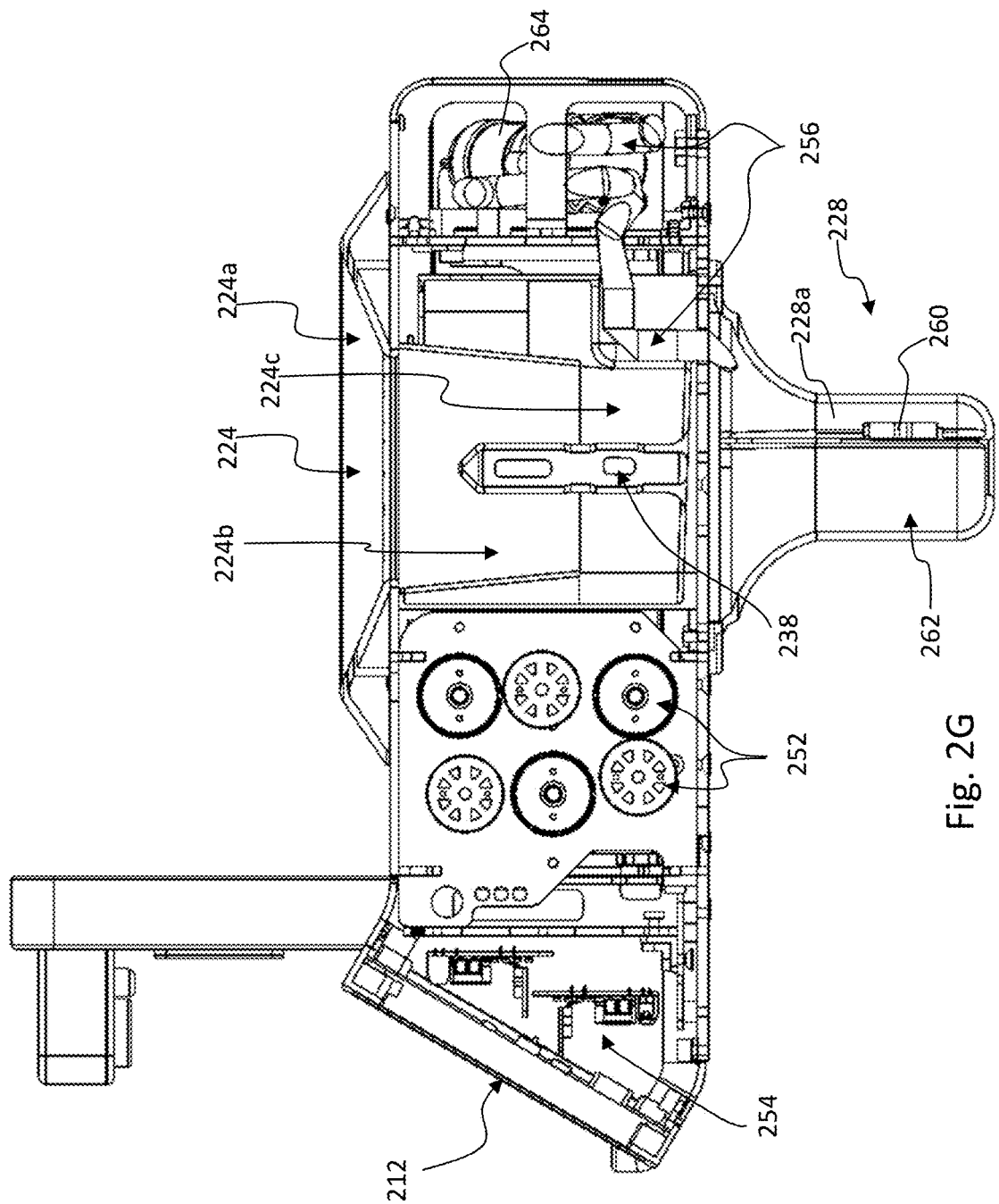

PERSONALIZED DIETARY SUPPLEMENT DISPENSING DEVICE

BACKGROUND

Field

The present disclosure relates to devices for dispensing personalized dietary supplement formulations for different users. More particularly, the present disclosure relates to dispenser devices that can be retrofit onto existing water bottle systems, water purification systems, water cooling systems, or from any water source and provide different users personalized dietary supplement formulations to provide a dietary supplement protocol over time.

Description of Related Art

Previously, beverage dispensing devices have been configured for providing predefined or stock compositions to consumers. While some dispensing devices allow the user to make some choices, such as flavor of soda (e.g., adding cherry to a cola beverage), the dispensing is still a predefined or stock composition. Some dispensing devices allow the consumer to make selections for different combinations of ingredients, which often is based on what the consumer "wants." However, prior dispensing devices have not been configured to provide the consumer with personalized dietary supplement compositions that are tailored for what the consumer needs based on consumer health information.

Thus, there is a need for a technology that can be used for dispensing personalized compositions that are tailored by the dispenser for the specific consumer based on what the consumer "needs" in view of their health information.

SUMMARY

In some embodiments, a dietary supplement dispenser can include: a water source inlet configured for receiving water; a plurality of supplement cartridges, each supplement cartridge including a supplement composition that is different from the other supplement compositions of the other cartridges; at least one dispenser fluidly coupled with the water source inlet and plurality of supplement cartridges; a formulation mechanism operably coupled with the water source inlet and the plurality of supplement cartridges, wherein the formulation mechanism is configured for regulating fluid flow from the water source inlet and the plurality of supplement cartridges to the at least one dispenser; an input device configured to receive input for a user; a dispenser controller operably coupled with the formulation mechanism and input device. The dispenser controller can be configured to: receive identification information input from a user via the input device; obtain a supplement dosage formulation for the user based on a dietary supplement protocol of the user; and control dispensing of water and at least one supplement composition of the plurality of supplement cartridges to provide the supplement dosage formulation to the user.

In some embodiments, a dietary supplement dispenser can include: a plurality of supplement cartridges, each supplement cartridge including a supplement composition that is different from the other supplement compositions of the other cartridges; at least one dispenser fluidly coupled with the plurality of supplement cartridges; a formulation mechanism operably coupled with the plurality of supplement cartridges, wherein the formulation mechanism is configured for regulating fluid flow from the plurality of supplement cartridges to the at least one dispenser; an input device configured to receive input from a user; a dispenser controller operably coupled with the formulation mechanism and input device, wherein the dispenser controller is configured to: receive identification information input from a user via the input device; obtain a supplement dosage formulation for the user based on a dietary supplement protocol of the user; and control dispensing of at least one supplement composition of the plurality of supplement cartridges to provide the supplement dosage formulation to the user. In some aspects, the supplement compositions can be dispensed with or without water. The dispenser may be configured to dispense the water into a cup or other container or into a food or any other consumable.

In some embodiments, a dietary supplement dispenser can include: a housing having a top region with a water bottle receiver and a bottom region with a water cooler receiver, thereby the housing being configured to fit between a water bottle and a water cooler (e.g., water bottle service cooler base); a water source inlet configured for receiving water from the water bottle receiver; a plurality of supplement cartridges, each supplement cartridge including a supplement composition that is different from the other supplement compositions of the other cartridges; at least one dispenser fluidly coupled with the water source inlet and plurality of supplement cartridges; a formulation mechanism operably coupled with the water source inlet and the plurality of supplement cartridges wherein the formulation mechanism is configured for regulating fluid flow from the water source inlet and the plurality of supplement cartridges to the at least one dispenser; and a dispenser controller operably coupled with the formulation mechanism, wherein the dispenser controller is configured to control dispensing of water and at least one supplement composition of the plurality of supplement cartridges to provide a supplement dosage formulation to the user from the at least one dispenser.

In some embodiments, a method of providing a dietary supplement can include: receiving identification information input from a user via the input device; obtaining a supplement dosage formulation for the user based on a dietary supplement protocol of the user; optionally providing water; providing a plurality of supplement cartridges, each supplement cartridge including a supplement composition that is different from the other supplement compositions of some of the other cartridges; optionally regulating fluid flow of the optional water to a water dispenser; regulating fluid flow of at least one supplement composition from the at least one supplement cartridge to at least one supplement dispenser; and controlled dispensing of the optional water and/or the at least one supplement composition of the plurality of supplement cartridges to provide the supplement dosage formulation to the user.

In some embodiments, a method can include: inputting identification information and heath information for a subject as input data into a computing system; analyzing the health information of the subject by processing the identification information and heath information through a nutritional model to generate a nutritional condition for the subject; identifying a health condition (e.g., homeostasis or improvement) in the nutritional model based on the nutritional condition of the subject; generating a dietary supplement protocol for the subject to change an initial nutritional condition toward the health condition (e.g., health improvement condition or health information improvement in subsequent health information); and determining a dosing regimen for a plurality of dietary supplements to be administered to the subject to achieve the change from the initial nutritional condition toward the health condition.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 2A-2H illustrate different views and perspectives of an embodiment of a dietary supplement dispenser: FIG. 2A is a perspective view; FIG. 2B is a front view; FIG. 2C is a side view; FIG. 2D is a top view; FIG. 2E is a bottom view; FIG. 2F is a bottom perspective view; FIG. 2G is a cross-sectional side view; and FIG. 2H is cross-section top-down view.

Figure 1:
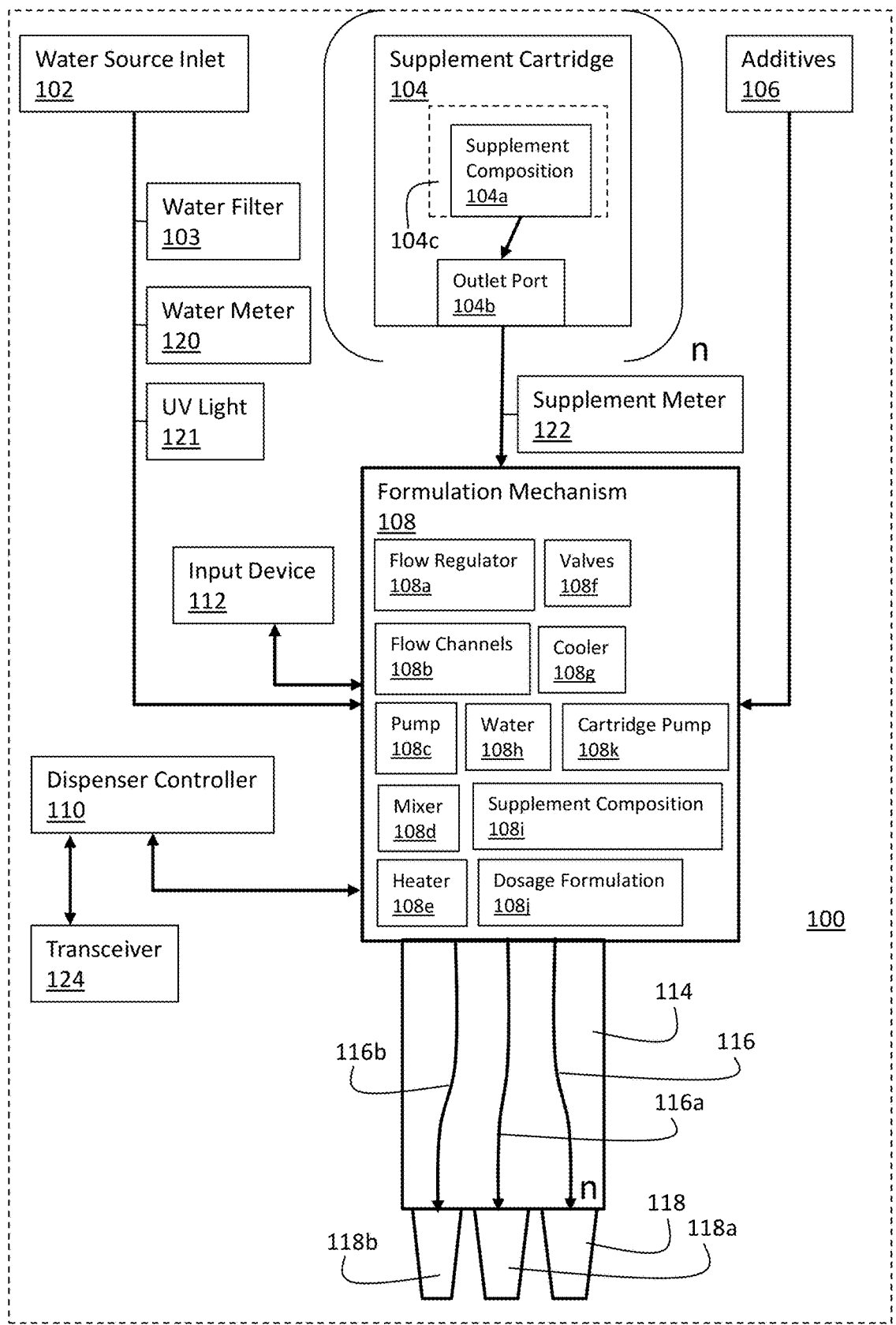
FIG. 1 illustrates an embodiment of a dietary supplement dispenser.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to a dispenser that is configured to dispense different supplement compositions to formulate a supplement dosage formulation. The dispenser can dispense water with one or more different supplement compositions to formulate the dosage. The supplement compositions can be retained in reservoirs within the dispenser, and dispensed on-command with the water. Each supplement composition can be in a cartridge that is removable or replaceable in the dispenser so that they can be exchanged when empty or as desired. The dispenser can have a separate dispenser nozzle for water and for each of the different supplement compositions. Separate dispensing lines for each composition and water can alleviate contamination of different supplement compositions when there is residue in a line and it gets dispensed when the composition is not supposed to. A cleaning cartridge with a cleaning composition (e.g., water, distilled water, purified water, optionally with a detergent or other cleaning composition) can be provided for cleaning each of the lines in the dispenser.

In some embodiments, the dispenser is a retrofit device that is adapted to work with existing water coolers. The dispenser can include a water bottle adapter configured to receive a water bottle that typically goes into the water cooler base. For example, the water bottle adapter can be a recess in a top of the dispenser that is dimensioned to receive the neck of a water bottle (e.g., water service water bottle such as 1, 2, 3, 4, 5, or more gallons). The dispenser can include a water cooler base adapter that is dimensioned as the size of a water bottle such that it fits like a water bottle into a water cooler base. That is, the dispenser fits where the water bottle usually fits, and thereby sites between the water bottle and the water cooler base. This configuration allows for the water cooler base to function to cool water and to dispense cooled water. The operations of the water cooler do not change with the retrofit dispenser. Instead, the functionality of the dispenser is added to the water cooler base.

In some embodiments, the dispenser only receives the water bottle and dispenses water and the supplement formulations. Here, the dispenser functions to dispense water with or without the supplement compositions. This dispenser includes the water bottle adapter but is devoid of the water cooler base adapter.

In some embodiments, the dispenser receives the water from an inline water source. Here, the dispenser does not include a water bottle adapter or a water cooler base adapter.

In some embodiments, the dispenser is devoid of any water inlet or water source. This dispenser only includes the supplement cartridges and only dispenses the supplement compositions as dosage formulations without adding any additional water. For example, such a dispenser can dispense the dosage formulation into a beverage (e.g., coffee, water, juice, etc.) or to a food or any other consumable.

In some embodiments, the dispenser is configured to monitor usage of water alone and supplement formulations. For example, the dispenser includes water meters that measure the amount of water used, such as per water dispensing and per user. The dispenser can also include a computerized controller that can process data and perform actions related to dispensing dosage formulations. This can include obtaining information for a user, obtaining a formulation for the user, or even determining a formulation for the user. The dispenser can also include a communications unit that is configured to communicate with a server over a network and report water and supplement usage back to a computing system, which can include a server, databases, and any computing units needed. The configuration of the controller turns the dispenser into a smart unit for hydration support, logistics support, etc. The controller also allows the dispenser to dispense personalized formulations for a personalized supplement program.

The present technology can also include a personalized supplement program, which can be used with or without the dispenser. That is, the personalized supplement program can be used with the dispensers described herein, or it could be adapted to be provided by other means. The personalized supplement program can formulate and provide custom supplement formulation for each user over time. The dispenser does not provide a customized beverage based on user selection or an individual beverage level. The dispenser does not have a stock of a number of different formulations it cycles through. Instead, each formulation dispensed to the user is a personalized formulation.

The personalized supplement program can include a dietary supplement protocol that includes one or more supplement dosing regimens, which further includes a plurality of individual dosage formulations. Each dosage formulation is personalized for the user. The personalization can be from user preference for dietary supplement and health goals. The personalization can also be from the user providing identification information and health information, which is then processed to determine the dietary supplement protocol, dosing regimens, and individual personalized dosage formulations. The user can fill out a questionnaire to provide information regarding health information, such as weight, height, age, gender, level of activity, typical diet, and the like. This information can be matched with their identification information (e.g., name, security number, login, etc.).

In some embodiments, the personalized supplement program can use health information that is obtained from an analysis of a biological fluid or biomarker of the subject. For example, the analysis can include proteomic, genomic, epigenomic, lipidomic, glycomic, foodomic, transcriptomics, metabolic, and others. The data can be obtained by any way possible, such as by analysis of gene genes, proteins, metabolites, lipids, hair, blood fluid chemistry, and the like.

In some embodiments, the personalized supplement program can use information about the user, such as historical health information. The information can be compared to new health information, such as obtained by monitoring or analyzing biological data of the user. The historical data can be compared to the monitored data (e.g., in response to a protocol), and then a dietary supplement protocol can be generated or modified based on the monitored data. Changes in the health information of a user can change subsequent dosage formulations for that user. The new health information can be obtained by biometric monitoring, such as pulse rate, respiration, temperature, blood pressure, sleep time, heart variability, and many others. Also, a history and current disease state or disorder can be considered, such as for example long term chronic conditions diabetes, heart, cholesterol, and many others.

In some embodiments, the environment and season can be used for determining the dietary supplement protocol and the individual personalized formulations. For example, the day of the month or year can be used to determine a formulation, such as an immune boost during cold, flu, or covid season. The time of day, such as morning, noon, afternoon, evening and night can be used to determine the formulation, where different times of the day can have different formulations. For example, lipid soluble supplements may be given at around noon but not at night, or vice versa. In another example, a noon formulation can give an energy boost to get the user through the afternoon. Of course, these changes area also accompanied by the overall protocol. Also, the ambient conditions, such as temperature, humidity, air quality, pollen count, source water quality, filtered water quality, or the like can be factored in determining the personalized dosage formulation. Population data may also be used, where different requirements may be in rural versus urban environment.

In some embodiments, a biometer can be used for monitoring the user, such as by a smart watch, which sends the health data to the system for use in determining the dosage formulation to be delivered to the user. The biometer can monitor metrics, such as activity monitoring (e.g., steps), exercise (e.g., heart rate), sleep, work, or sitting, which can be considered when determining the personalized dosage formulation.

In some embodiments, the system can perform a study on the user by identifying a health status in or more categories, providing specific dosage formulations over time, and assessing any changes in the health statuses. Positive improvements can be used to identify supplements or formulations advantageous to the user. Negative or declining health statuses can be used to identify supplements or formulations to void. The method is performed as a study of one user. The system performs a blind study on a user to optimize health parameters by modulating and tracking formulations and then tracking the user's response thereto. The blind study tests supplements and combinations while monitoring health parameters and user feedback. The system automatically tunes supplements for performance parameters, such as sleep and sleep stages, speed of falling asleep, alertness, user reported awareness, and many others. This helps identify personalized formulations for each user.

FIG. 1 illustrates a schematic diagram of an embodiment of a dietary supplement dispenser 100. The dietary supplement dispenser 100 includes a water source inlet 102 configured for receiving water. The water source inlet 102 can be configured to be coupled to any type of water source. For example, the water source inlet 102 can be adapted to be coupled to a water bottle (e.g., large water service bottle), a water line (e.g., water utility), a water dispenser, a water cooler, a water heater, a filtration unit, any other water source, and combinations thereof. The water source inlet 102 can include any type of coupling or fastener that is used in fluidics, such as by gravity, friction, threading, clamping, collaring, snapping, or any ither type of fastening.

Figure 3:
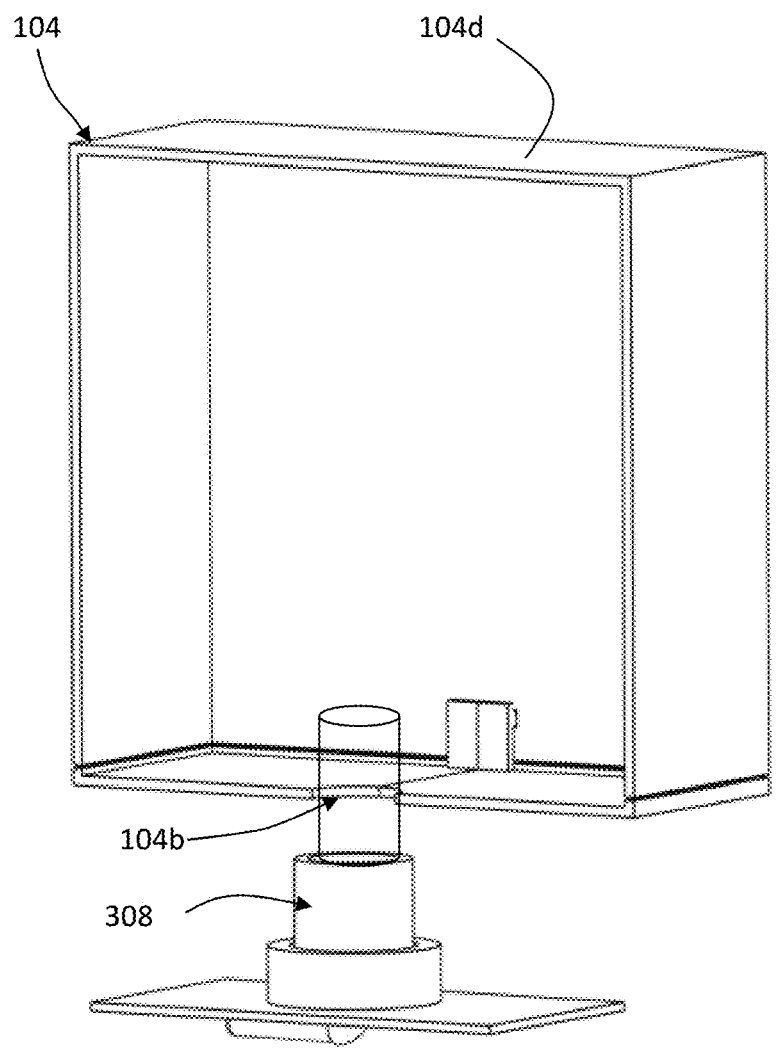
FIG. 3 illustrates a cross-section view of an example of a cartridge of the dietary supplement dispenser.

The dietary supplement dispenser 100 includes a plurality of supplement cartridges 104 (e.g., "n" cartridges, where "n" is an integer). Each supplement cartridge includes a supplement composition 104a that has one or more supplements. The supplement composition can be formulated to have supplements for a dietary supplement regimen that is adapted to provide supplemental dosage formulations to one or more different users. In some aspects, the supplement compositions can be obtained from a standard catalog of supplement compositions that can be selected or identified to fit a supplement regimen. In other aspects, the supplement compositions can be formulated for a particular user as part of a multi-composition combination. In some aspects, each cartridge includes a supplement composition 104a that is different from the other supplement compositions 104a of the other cartridges 104. The supplement composition 104a can be retained within a supplement reservoir 104c, such as a bladder or collapsible plastic or foil pouch. The cartridges 104 can include an outlet port 104b that is fluidly coupled with the supplement reservoir 104c. FIG. 3 shows a cross-section view of an example of the cartridge 104 having a body 104d that is dimensioned for containing the supplement reservoir 104c that is fluidly couplable with the outlet port 104b, where the outlet port 104b is coupled to a flow channel 308, which can be part of the flow channels 108b of the formulation mechanism 108.

The dietary supplement dispenser 100 includes at least one dispenser 114 fluidly coupled with the water source inlet 102 and plurality of supplement cartridges 104. The dispenser 100 can include a dispenser head 240 protruding from a dispenser arm 232 (see FIG. 2A). The dispenser arm 232 also includes a dispenser button 234 that can be used for dispensing water or a supplement dosage formulation when pressed or otherwise triggered. The dispenser head 240 can include an underside or down-pointing region that has the at least one dispenser 114. As shown in FIG. 2F, dispenser 114 can include a water dispenser 118a and a plurality of supplement dispensers 118b, where six supplement dispensers 118b are shown to be positioned around the water dispenser 118a. Each dispenser 118 can be configured with a nozzle for aiming the trajectory of the dispensed liquid. The water dispenser 118a and plurality of supplement dispensers 118b can be arranged close together to aim into the same receiver, such as a glass, mug, or other liquid container. The dispenser 114 is also shown to include flow channels 116 for water and the supplement composition 104a. The flow channels 116 can include a water flow channel 116a and a plurality (e.g., six) supplement flow channels 116b, which are fluidly coupled to the dispensers 118.

The dietary supplement dispenser 100 includes a formulation mechanism 108 that is operably coupled with the water source inlet 102 and the plurality of supplement cartridges 104. The formulation mechanism 108 includes all of the different components, pumps, valves, channels, and controllers that operate together to dispense water and the appropriate supplement composition(s) to provide a supplement dosage formulation to the user. The formulation mechanism 108 is configured for regulating fluid flow from the water source inlet 102 and the plurality of supplement cartridges 104 to the dispenser 114. The formulation mechanism includes at least one: flow regulator 108a; flow channel 108b; pump 108c; cartridge pump 108k for each supplemental cartridge 104; mixer 108d; heater 108e; valve 108f; cooler 108g; water 108h from the water source 102; supplement composition 108i from the at least one cartridge 104; and/or dosage formulation 108j as a mixture from the water and at least one supplement composition. These components can be in various arrangements and combinations to provide the water and supplement compositions 104a to the dispenser 114, such as unique fluidic pathways between each cartridge 104 or water source to the unique dispenser 118, such as water dispenser 118a or any of the different supplement dispensers 118b. In some aspects, a mixer 108d is omitted when each liquid is dispensed through a separate dispenser 118 such that there is no mixing of the supplement compositions with each other and/or with water before being dispensed from the dispenser 114.

The dietary supplement dispenser 100 includes an input device 112 configured to receive input from a user. The input device 112 can be any type of input device where the user can manually enter input data or can transmit or otherwise provide data to the dispenser 100. The input device 112 can be configured as a touch screen as shown; however, the input device 112 may include a combination of a touch screen or wireless data receiver to provide input from the user. The touch screen embodiment can be configured to provide viewable display icons for selections or a keyboard, and may display any common input display graphics with selectable options.

The dietary supplement dispenser 100 includes a dispenser controller 110 operably coupled with the formulation mechanism 108 and input device 112. The dispenser controller 110 can be configured as a computer or any computing device that has a processor that can process data and perform normal computing operations for operation of the dispenser 100 as well as receive and process input data from the input device. In addition to many operations, the dispenser controller 110 is configured to receive identification information input from a user via the input device 112. This allows the dispenser controller 110 to use the identification information of a user to access a dietary supplement protocol or particular dietary supplement regimen over a period of time to provide a customized personal supplement dosage formulation to the user for each dose. Accordingly, the dispenser controller 110 can obtain a supplement dosage formulation for the user based on a dietary supplement protocol of the user. For example, the dietary supplement protocol for the user may be stored locally in a non-transitory memory device or remotely in a database accessible over a network or through a server. Once the supplement dosage formulation for a particular dose is determined or identified, the dispenser controller 110 can control dispensing of water and at least one supplement composition 104a of the plurality of supplement cartridges 104 to provide the supplement dosage formulation to the user.

The dietary supplement dispenser 100 can include a water meter 120 operably coupled with the water source inlet 102. The water meter 120 can collect water flow data (e.g., volume, flow rate, etc.) to determine the amount of water flow used for one or more formulations, or track the water being used for one or more formulations for a specific user. The dispenser controller 110 can be configured for receiving the water meter data and monitoring water usage by at least one user and tracking water usage for the at least one user over a time period with the water meter.

The dietary supplement dispenser 100 can include at least one supplement meter 122 operably coupled with a supplement reservoir 104c having the supplement composition 104a of each supplement cartridge 104. That is, the supplement meter 122 is positioned and configured to collect supplement flow data (e.g., volume, flow rate, etc.) to determine the amount of each supplement being used, such as for one or more users. The dispenser controller 110 is configured for receiving the supplement meter data and monitoring supplement usage by at least one user and tracking supplement usage for the at least one user over a time period for each supplement composition 104a.

The dietary supplement dispenser 100 can include a transceiver 124 operably coupled with the dispenser controller 110 and configured to communicate over a network 126. The transceiver 124 can be any type of wireless or optical transceiver that can send data through a network (e.g., send user identification data or user water usage data or user supplement usage data) or receive data through a network (e.g., receive the supplemental dosage formulation or the dietary supplement protocol for each user. The transceiver 124 can also be used to transmit identification information for at least one user to a dietary supplement protocol server 128 and configured to receive the supplement dosage formulation of a dietary supplement protocol for the at least one user from the dietary supplement protocol server 128 (e.g., FIG. 5).

The dietary supplement dispenser 100 can include a dispenser controller 110 that is operably coupled to at least one additive reservoir 106. Each additive reservoir can have one or more additives for formulating the supplement dosage form. For example, the additive can balance pH, improve solubility or mixing of different supplements, provide for an emulsion or micelle formation, or any other additive or formulation action. The dispenser controller 110 can be configured to determine at least one additive to be included in the supplement dosage formulation and control dispensing of the at least one additive to provide the supplement dosage formulation to the user.

Figure 2A:
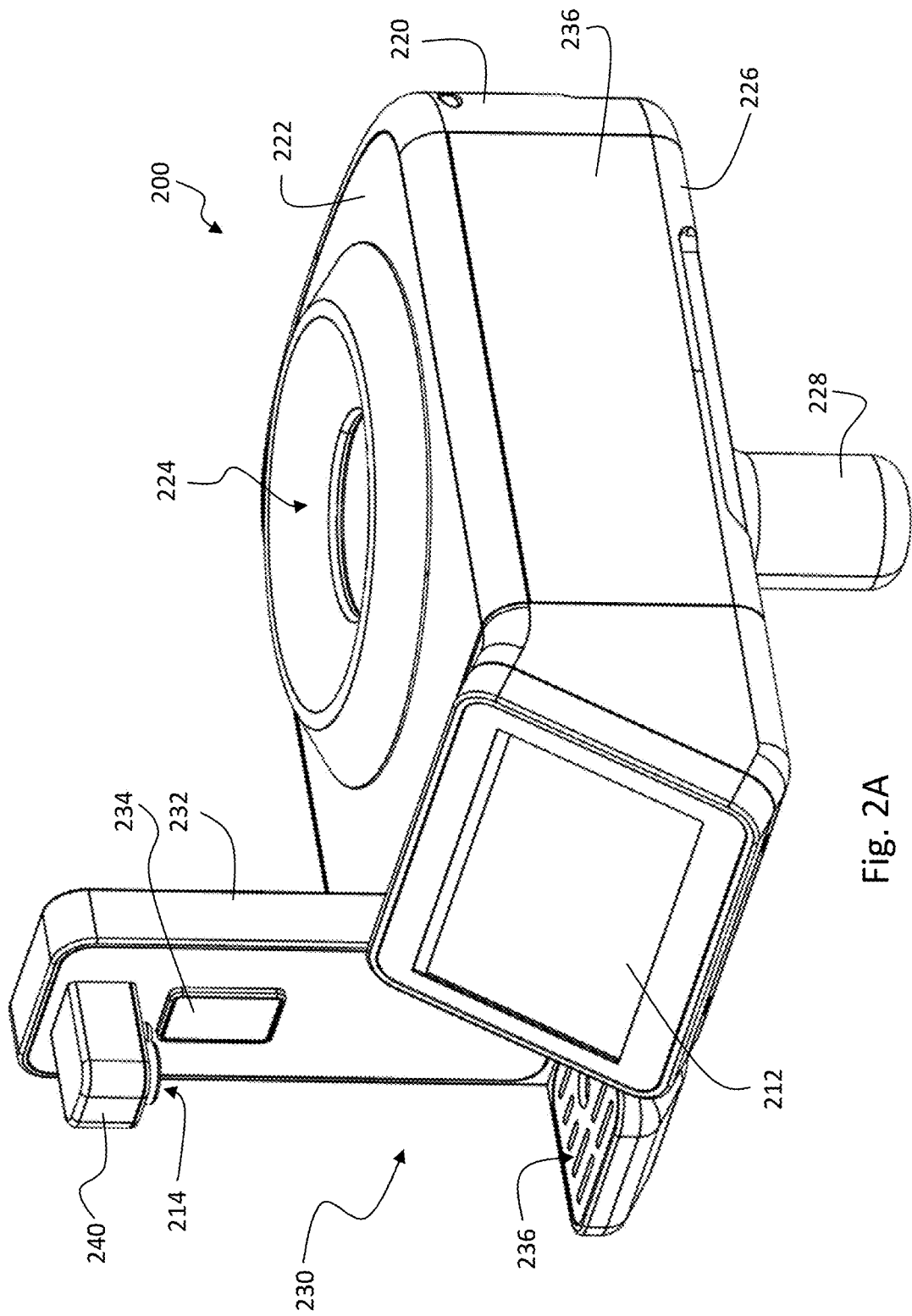
Figure 2B:
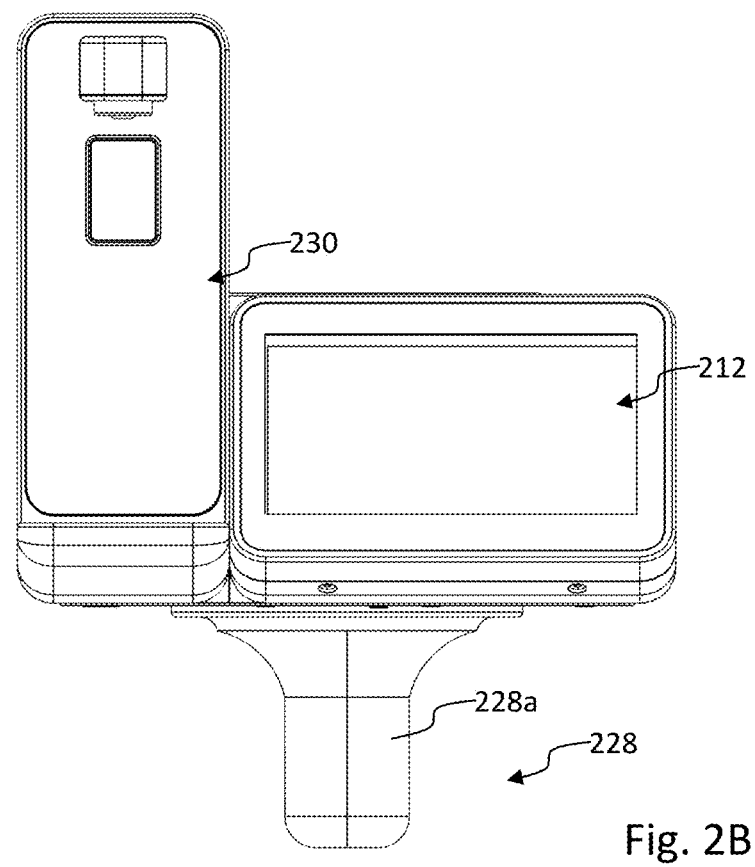
Figure 2C:
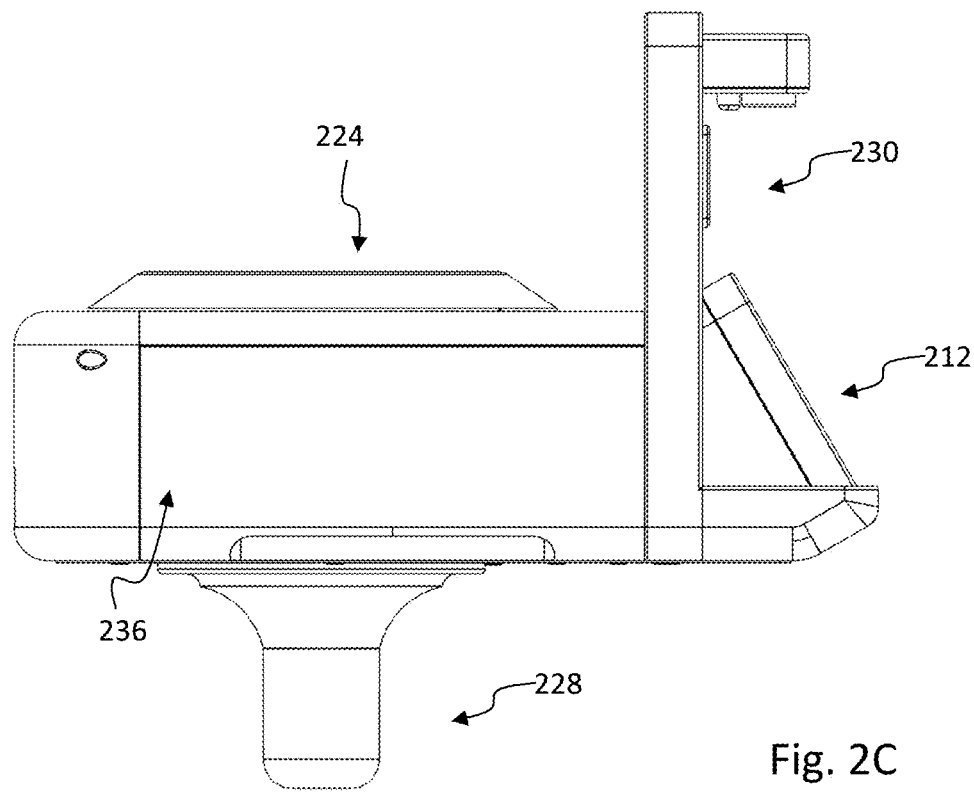
Figure 2D:
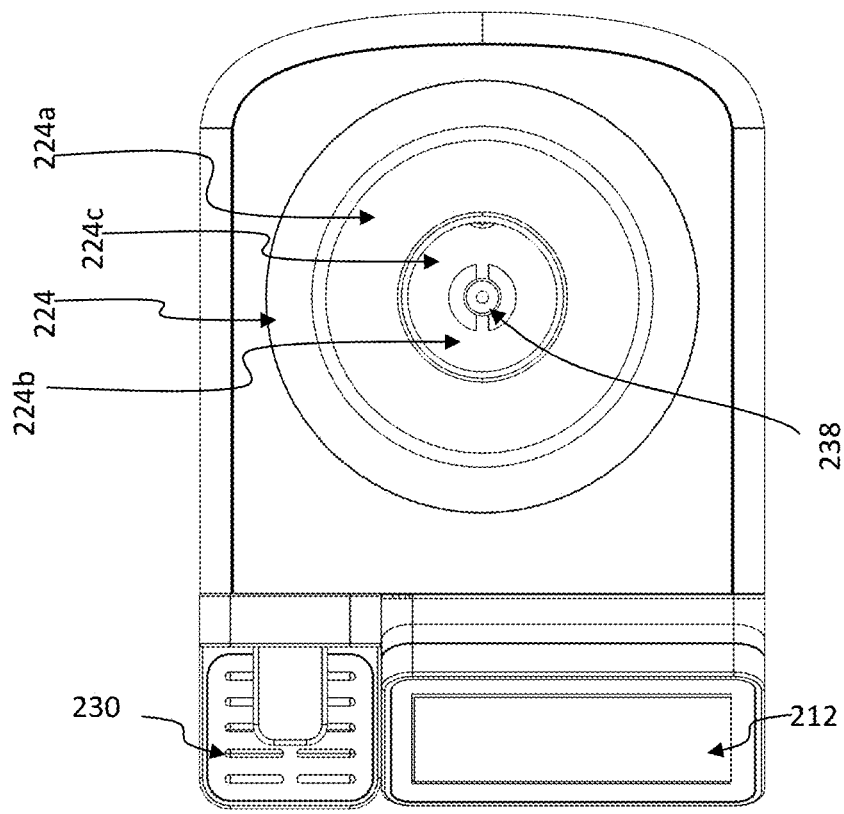
Figure 2E:
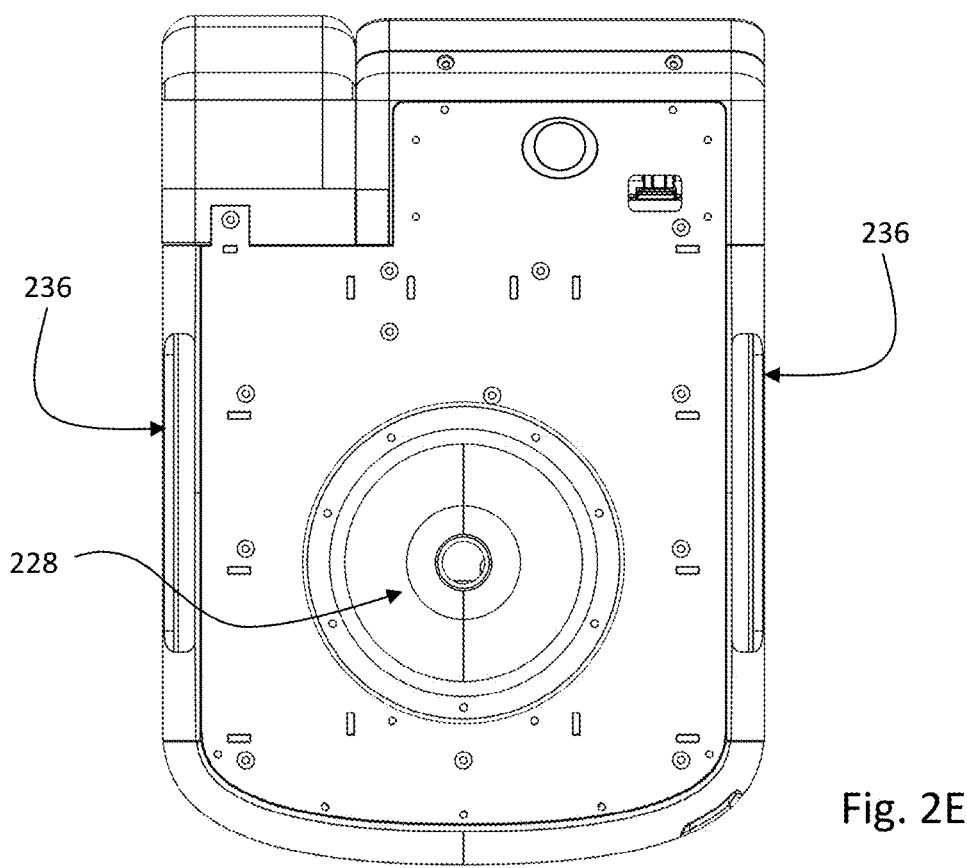
Figure 2F:
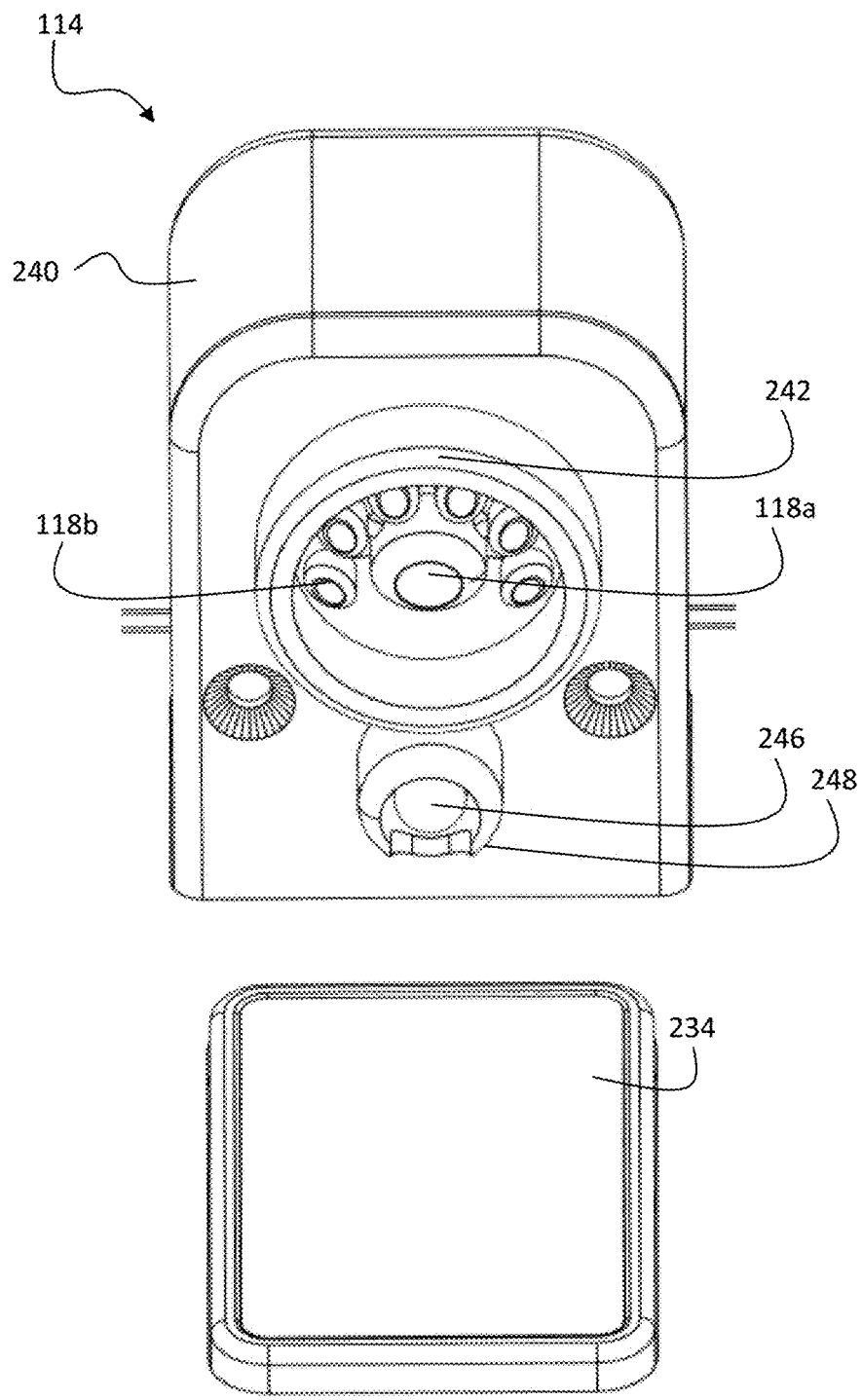
Figure 2H:
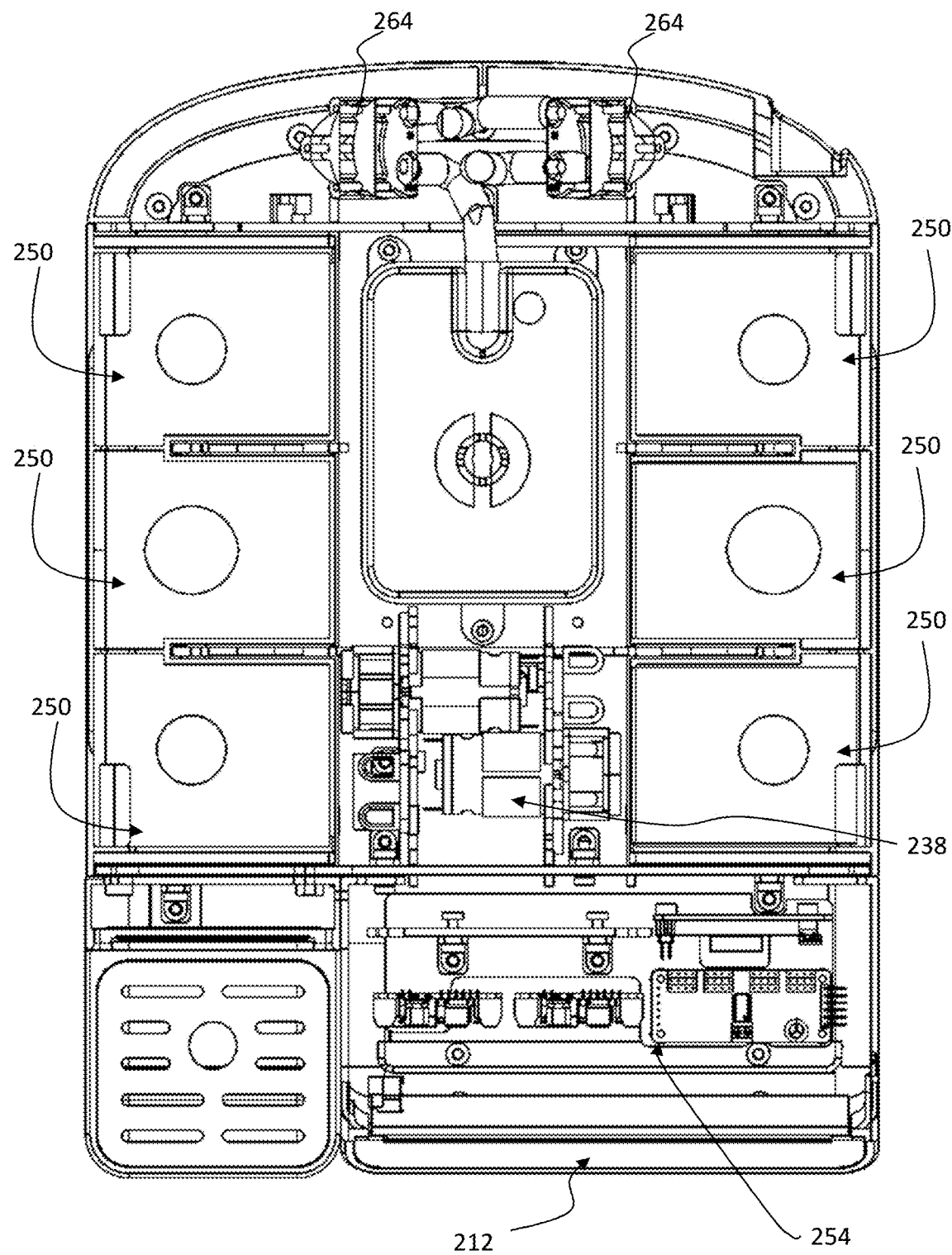

The dietary supplement dispenser 100 can include a port 250 for each supplement cartridge as shown in FIG. 2H. Each port 250 can configured for removably receiving the respective supplement cartridge 104 therein and fluidly coupling with the supplement composition 104a. Each port 250 can be operably coupled with a flow channel 308 (FIG. 3) that is connected to the appropriate dispenser 118.

The dietary supplement dispenser 100 can include at last one dispenser 114 that includes at least one nozzle 118 that is configured as at least one of: a water only nozzle (e.g., 118a), a supplement only nozzle (e.g., 118b) for at least one supplement composition 104a, a supplement only nozzle for each supplement composition 104a, and a water and supplement combination nozzle.

Figure 5:
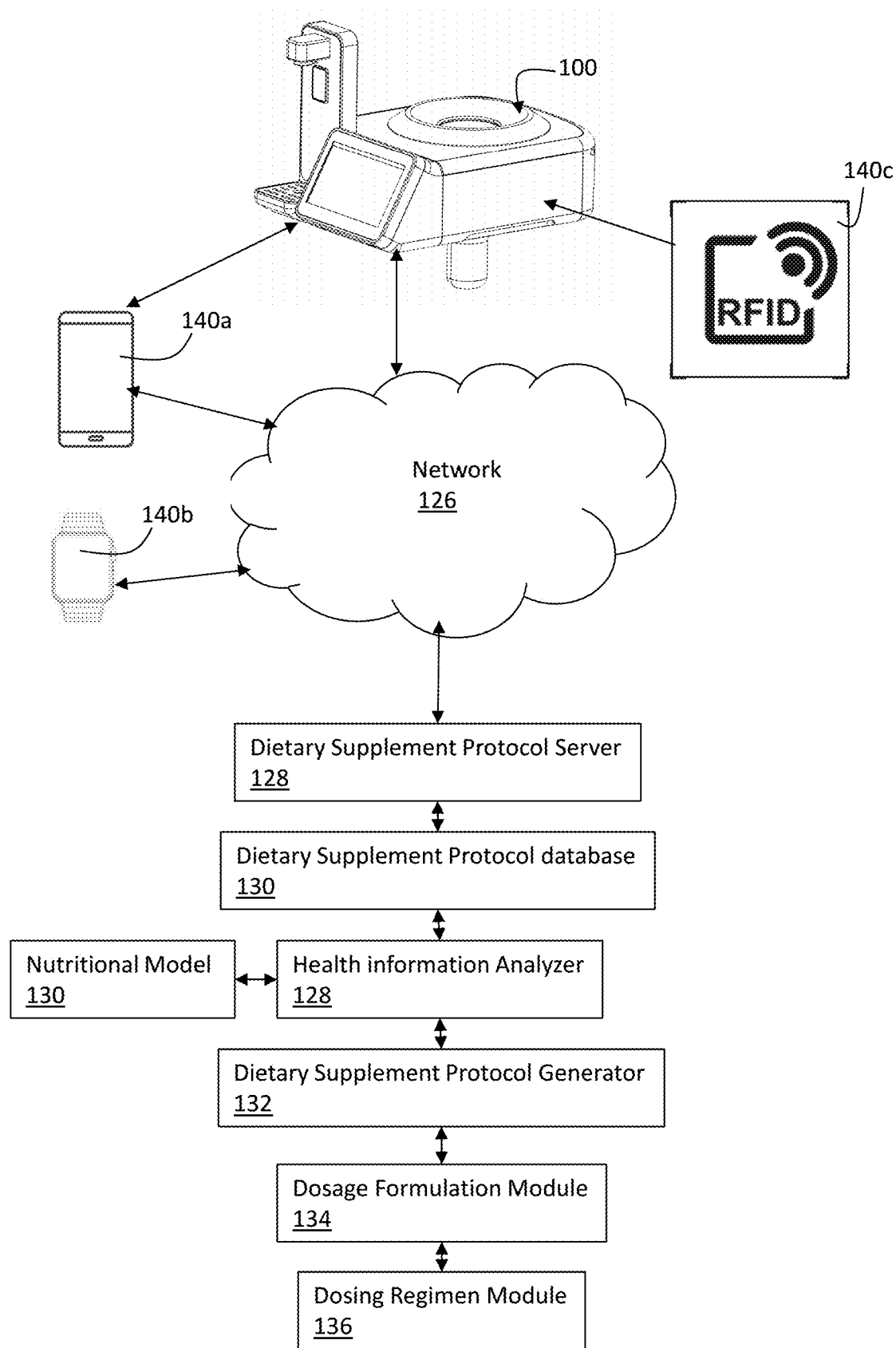
FIG. 5 shows an operational environment for the dispenser.

The dietary supplement dispenser 100 can include a wireless input device 112 that is configured to receive a wireless signal from a wireless device 140 of the user. FIG. 5 shows the wireless input device 112 can be configured to communicate with a device 140 being a mobile phone 140a (e.g., smart phone) or a smart watch 140b. In some examples, the signal received by the input device 112 can be a signal from a mobile device, WiFi module, Bluetooth module, RFID tag 140c (e.g., FIG. 5), near field communication tag, or other signal provider designated to the user.

The dietary supplement dispenser 100 can include an input device 112 is configured to receive manual data input from the user. In some aspects, the input device 112 includes a touch screen (e.g., as shown), display, keyboard, mouse, microphone, camera, scanner, or combination thereof.

The dietary supplement dispenser 100 can include at least one water filter 103 fluidly coupled with the water source inlet 102 upstream of the formulation mechanism 108. The water filter 103 can be positioned to filter the water received from the water source inlet 102, which can be helpful if the water is municipality water or other water that may be advantageously filtered. The water filter 103 can be installed in a water filtration unit, such as those that are commonly used in water filtration applications.

The dietary supplement dispenser 100 can include a water source inlet 102 that is configured to be fluidly coupled with a water source selected from the group consisting of: a water container; a water line; a water dispenser; a water cooler; a water heater; a filtration unit; and combinations thereof. That is, the water source inlet 102 can have the proper fittings, tubes, fasteners, pumps, valves or other common water provisioning components.

The dietary supplement dispenser 100 can include comprising a UV light 121 (e.g., UV-C light) that is configured for irradiating the water upstream of the at least one dispenser 114. That is the UV light 121 can be upstream of the formulation mechanism 108 as shown, or within the formulation mechanism 108.

The dietary supplement dispenser 100 can include a formulation mechanism 108 that has: at least one pump 108c operably coupled with the water source 102 and a water dispenser 118a of the at least one dispenser 114; a cartridge pump 108k coupled to each supplement cartridge 104 and a supplement dispenser 118b of the at least one dispenser 114; at least one water flow channel 108b; and a plurality of supplement cartridge flow channels 108b that are fluidly isolated from each water flow channel 108b.

In some embodiments, the dietary supplement dispenser 100 can include a dispenser controller 110 that is configured to control dispensing of the water and each supplement composition 104a from separate dispensers 118 so as to deliver the supplement dosage formulation to the user (FIG. 2F). This allows for the supplement dosage formulation to be formulated within the container that the dispenser 114 is dispensing into.

FIGS. 2A-2H illustrate different views and perspectives of an embodiment of a dietary supplement dispenser 200. As shown, a dietary supplement dispenser 200 can include a housing 220 having a top region 222 with a water bottle receiver 224. The dietary supplement dispenser 200 can also include a bottom region 226 with a water bottle stand receiver 228. The water bottle receiver 224 and water bottle base receiver 228 allow for the housing 220 to be configured to fit between a water bottle and a water cooler base (e.g., office water cooler). Accordingly, the dispenser 200 includes a water source inlet 102 configured for receiving water from the water bottle receiver 224.

In some embodiments, the water bottle receiver 224 includes an upper receiver 224a configured for receiving the shoulders of a water bottle and a lower receiver 224b for receiving the neck and opening of the water bottle therein. The lower receiver 224b includes a reservoir region 224c where the water is provided from the bottle. The reservoir region 224c includes a water intake 238 (e.g., opening in a protruding tube) configured as the water source inlet 102.

The dietary supplement dispenser 200 includes a plurality of supplement cartridges 104. Each supplement cartridge 104 can include a supplement composition 104a that is different from the other supplement compositions 104a of the other cartridges 104.

The dietary supplement dispenser 200 includes at least one dispenser 214 fluidly coupled with the water source inlet 102 and plurality of supplement cartridges 104.

The dietary supplement dispenser 200 includes a formulation mechanism 108 operably coupled with the water source inlet 102 and the plurality of supplement cartridges 104. The formulation mechanism 108 is configured for regulating fluid flow from the water source inlet 102 and the plurality of supplement cartridges 104 to the at least one dispenser 214.

The dietary supplement dispenser 200 includes a dispenser controller 110 operably coupled with the formulation mechanism 108. The dispenser controller 110 can be configured to control dispensing of water and at least one supplement composition 104a of the plurality of supplement cartridges 104 to provide a supplement dosage formulation to the user from the at least one dispenser 114.

As shown in FIG. 2A, the dietary supplement dispenser 100 can include a dispensing station 230 having a dispensing arm 232 with the at least one dispenser 214 and a receiving platform 236. The dispensing arm 232 has a flow channel for the water and a flow channel for each supplement cartridge 104. The dispensing arm 232 has a dispenser button 234, which can include a light emitter or a reflector that reflects light.

As shown in FIG. 2A, the housing 202 includes a housing door 236 configured to be opened to access the plurality of supplement cartridges 104. Additionally, FIG. 2C shows another a housing door 236 configured to be opened to access the plurality of supplement cartridges 104, which is opposite of the other housing door 236. This allows for some of the cartridges 140 to be in ports 250 on one side of the housing 202 and some to of the cartridges 140 to be in ports 250 on the other side of the housing 202. FIG. 2H with three ports 250 on each side of the housing 202.

In some embodiments, the input device 212 includes a touch screen and is configured to receive input from a user. The dispenser controller 110 is operably coupled with the input device 212 to receive input data therefrom. The input data is used by the dispenser controller 110 to determine control instructions for controlling the formulation mechanism 108. The dispenser controller 110 is configured to: receive identification information input from a user via the touchscreen of the input device 212; obtain a supplement dosage formulation for the user based on a dietary supplement protocol of the user, which can be obtained from a local memory device of the dispenser 200 or at a server 128 or database 130 (FIG. 5); and control dispensing of water separately from each at least one supplement composition 104a of the plurality of supplement cartridges 104 to provide the supplement dosage formulation to the user.

In some embodiments, the housing 220 has a top region 222 with a water bottle receiver 224. As such, the housing 220 can be configured to receive a gravity-fed water bottle. In some aspects, the top region 222 has a recess 224a that forms the water bottle receiver 224, and the bottom region 226 has a protrusion 228a that forms the water bottle stand receiver 228 (e.g., protrusion receiver).

FIG. 2B shows a front view of the dispenser 200, where the dispensing station 230, touchscreen input device 212 and the water bottle stand receiver 228 are shown.

FIG. 2C shows a side view of the dispenser 200, where the dispensing station 230, touchscreen input device 212, water bottle receiver 224, and the water bottle stand receiver 228 are shown.

FIG. 2D shows a top view of the dispenser 200, where the water bottle receiver 224 and a water intake 238 (e.g., opening in a protruding tube). The water intake 238 can be configured as a tubular member that protrudes from the bottom of the water bottle receiver 224 and has at least one opening for receiving water therein and a conduit for passing the water to the formulation mechanism. FIG. 2E shows a bottom view of the dispenser 200.

While not shown, a backside of the dispenser 200 includes an electrical power plug adapter. However, it is contemplated that the dispenser 200 can be configured to run on battery power, where a battery pack can be included within the housing (not shown).

FIG. 2F shows a bottom perspective view of the dispensing station 230. This view shows the dispenser head 240 having the water dispenser nozzle 118a and the six different supplement nozzles 118b. The different supplement nozzles 118b can be arranged in any way or spacing relative to the water dispenser nozzle 118a. As shown, an annular protective rim 242 protrudes from the bottom surface and surrounds the nozzles 118a,b. Fastener locations 244 are also shown, which are used to assemble the dispenser head 240.

The dispenser head 240 is also shown to include a light emitter 246, which can be positioned near the nozzles 118a,b but outside of the annular protective rim 242. As such, the annular protective rim 242 protects the light emitter 246 from splashes during dispensing liquids. The light emitter 246 can be operably coupled with the dispenser controller 110 and configured to display different color lights in different patterns. The different colors and/or different light sequence patterns can provide information to the user. For example, the light can change colors (e.g., red to green) or provide a specific illumination color (e.g., green) to indicate a change from a stopped operation to a dispensing operation. The dispenser button 234 can include a reflective coating that reflects the light from the light emitter 246. However, the dispenser button 234 may be configured with a light emitter that can change the color of the button or ring around the button, or other color change. An embodiment can include the light emitter 246 and the dispenser button 234 having a light emitter in it, with or without also having the reflective surface. This can allow for multiple core and perimeter color combinations. In some aspects, the light emitters are used for entertainment or ambiance to provide an atmosphere for the user. For example, a calming formulation can be accompanied by a green or blue color, while an energetic formulation can be accompanied with an orange or red light.

The light emitter 246 may also include an annular protective rim 248 that protects the light emitter, and where optionally a cutout is included for directing light to the button 234.

FIG. 2G includes a cross-sectional side view showing the internal parts and compartments within the housing 202. Particularly, six pumps 252 are shown, which are fluidly coupled through tubes (e.g., fluid conduits) to the supplement cartridges 140 to pump supplement composition 140a to the dispensers 118b. Also, electric parts and circuit boards 254 that operate the touchscreen are also shown. Various tubing conduits 256 are shown to provide for the water fluid network separate from the supplement fluid networks.

FIG. 2G also shows the bottom region 226 has a protrusion 228a that forms the water bottle base receiver 228 (e.g., protrusion receiver). Inside the protrusion, there is a water sensor 260 that is configured to determine the water level in a lower reservoir 262 that feeds water to the water bottle stand that is receiving the water bottle stand receiver 228. The water sensor 260 senses the water level inside the lower reservoir and provides the water level data to the dispenser controller 110. Then, the dispenser controller 110 operates a water pump 264 that pumps water from the reservoir region 224c through tubing conduits 256 and into the lower reservoir 262. This allows for the water cooler that has the retrofit dispenser 200 coupled thereto to still be operated as a water cooler that dispenses cooled water. Thus, the option of cooled water or supplement dosage formulation can be made with a water cooler having the retrofit dispenser 200 between the cooler part and the large water bottle.

FIG. 2H is a top-down cross-sectional view that shows the ports 250 that receive the cartridges 104. Also, the water pumps 264 are shown, which includes one water pump to dispense water at the water dispenser 118a, and one water pump to dispense water into the lower reservoir 262.

FIG. 3 shows that the cartridges 104 can have a body 104d that has a chamber configured to receive a supplement composition 104 therein. The supplement composition 104a can be retained within the supplement reservoir 104c. The supplement reservoir 104c can include an outlet port 104b that is fluidly coupled with the supplement reservoir 104c. FIG. 3 shows a cross-section view of an example of the cartridge 104 having the body 104d that is dimensioned for containing the supplement reservoir 104c that is fluidly couplable with the outlet port 104b, where the outlet port 104b is coupled to a flow channel 308, which can be part of the flow channels 108b of the formulation mechanism 108. The supplement composition 104a can be retained within a supplement reservoir 104c, such as a bladder or collapsible plastic or foil pouch. The reservoir 104c can collapse as supplement composition 104a is dispensed therefrom, such that a void or headspace is not formed within the reservoir. This helps preserve the supplement composition 104a.

Figure 4A:
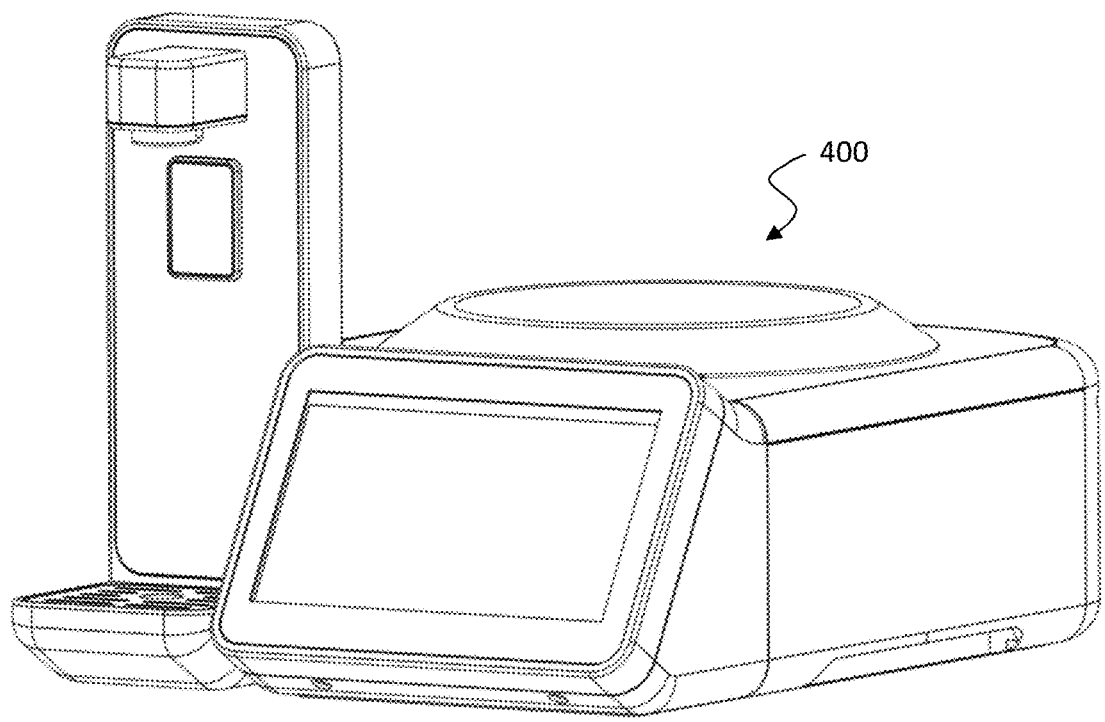
FIG. 4A illustrates a dietary supplement dispenser device that is configured to receive a water bottle and function as a water dispenser stand.

FIG. 4A illustrates a dietary supplement dispenser device 400 that is configured to receive a water bottle and function as a water dispenser stand. That is, the dietary supplement dispenser device 400 is configured to receive water from a bottle and dispense it from the dispenser, but it does not provide water from the bottle to a separate water cooler base. The dietary supplement dispenser device 400 can be considered to be a desktop version or it can have legs and operate as a standalone dispenser device that uses top mounted large water bottles (e.g., water service bottles). As such, the dietary supplement dispenser device 402 omits the water stand receiver.

Figure 4B:
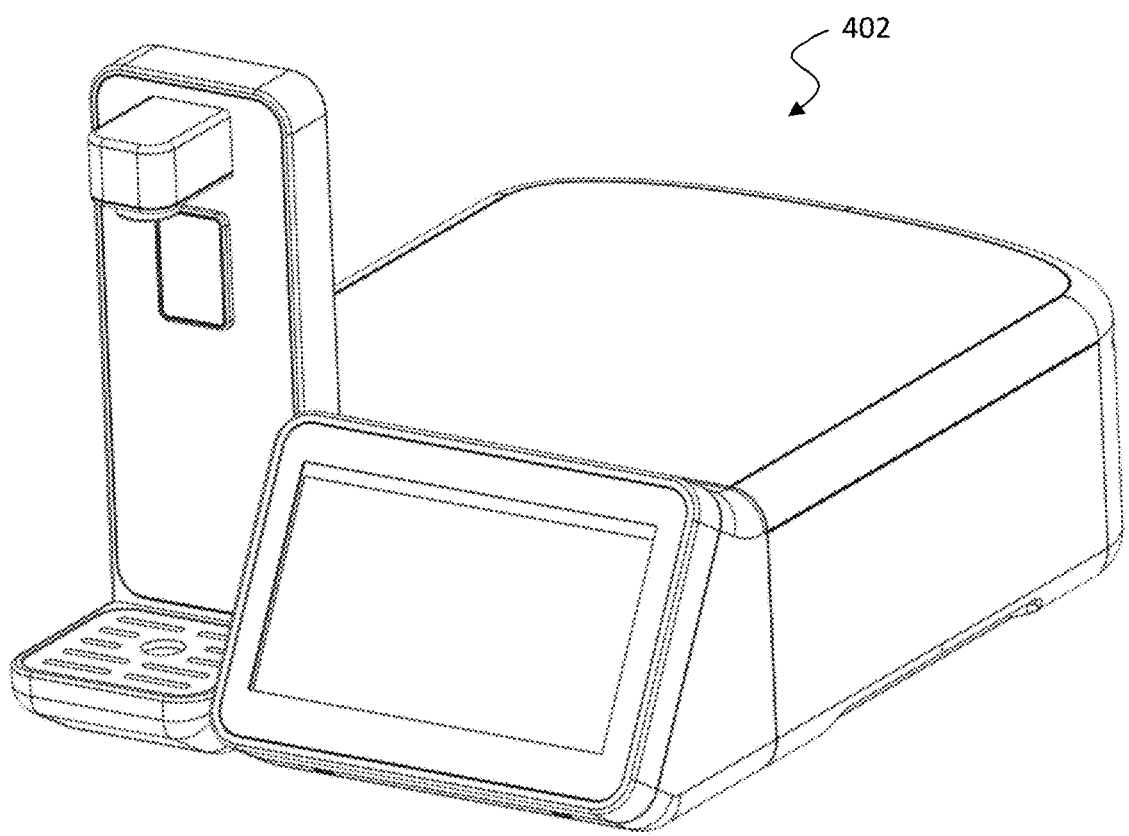
FIG. 4B illustrates a dietary supplement dispenser device that is configured to receive water from a water line (e.g., at the back side), which can allow for a continuous water supply.

FIG. 4B illustrates a dietary supplement dispenser device 402 that is configured to receive water from a water line (e.g., not shown at back of housing), which can allow for a continuous water supply. As such, the dietary supplement dispenser device 402 omits the water bottle receiver and the water stand receiver.

FIG. 4B may also be interpreted to illustrate an embodiment devoid of a water source inlet. This embodiment may dispense only the supplement compositions into a beverage, food, or other consumable.

FIG. 5 shows an operational environment for the dispenser 100. The environment shows an example of how the dispenser is used in a method of providing a dietary supplement.

In some embodiments, the user can approach the dispenser 100 and a mobile phone 140a or a smart watch 140b may communicate with the dispenser 100 and provide identification information of the user. This can allow for the dispenser 100 to determine the supplement dosage formulation that the user should receive. Alternatively, the user can include a signal tag 140c, such as RFID or a near field communication tag that can be read by the input device of the dispenser 100, which allows the dispenser 100 to identify the user and obtain identification information of the user.

The dispenser 100 is configured with the transceiver to communicate via a network 126 to a dietary supplement protocol server 128. The server 128 can be part of a computing network that operates with the personalized dynamic dietary supplement protocol. The dietary supplement protocol server 128 can communicate with a dietary supplement protocol database 130 that has a unique dietary supplement protocol for each user. The dietary supplement protocol can include the information for preparing one or more supplement dosage formulations for a dosage regimen. The dietary supplement protocol database 130 can receive the personalized protocols from a health information analyzer 128. The heath information analyzer 128 is configured for analyzing user data, such as identification and health information, and comparing the same with a model or processed with an algorithm in facilitating the generation of the protocol. The health information analyzer 128 can be configured with an algorithm or model for analyzing the health information of the subject by processing the identification information and heath information through a nutritional model to generate a nutritional condition for the subject user. The health information analyzer 128 can be adapted for identifying a health condition in the nutritional model based on the nutritional condition of the subject. This improvement in condition can be used as the basis for the determination of the protocol. The condition may need improvement in health, disease state, vitality, stress, sleep, energy, or the like, where a need for improvement can be determined. The need for improvement can be used for determining the dosage formulations to provide to the user to get the improvement.

The health information analyzer 128 can use a nutritional model 130, such by computation with an algorithm, to determine the health condition of the subject user. Then the nutritional model 130 can identify a nutritional improvement that can provide a physiological improvement to the subject user. The nutritional improvement can then be used to determine one or more supplements for obtaining an improvement in condition in the subject user. The one or more supplements can be identified as part of a dosage formulation for being administered to the subject user, where the dosage formulation can be part of an overall dietary supplement protocol for improving the condition in the subject.

The dietary supplement protocol generator 132 can obtain the data from the health information analyzer, and then generate the dietary supplement protocol for the subject user. The generator 132 may or may not be part of the health information analyzer 128, by being in the same computational module or in separate modules. The generator 132 can be configured for receiving output data from processing with the model 130 and generating the protocol for the user subject. This can include generating the overall protocol for achieving the health condition, such as improvement or homeostasis. The generator 132 is configured for generating a dietary supplement protocol for the subject to change an initial nutritional condition toward the health condition. The generator 132 can be operably coupled with or include a dosage formulation module 134 and a dosing regimen module 136. The dosing formulation module 134 can be used to generate each personalized dietary supplement dosage formulation for the subject user based on the input data and processing with the nutritional model 130. The dosing regimen module 136 can be used to generate a regimen for administration of the dietary supplement dosage formulations to the subject in order to achieve the overall protocol. The dosage formulation module 134 and dosing regimen module 136 can be configured for determining a dosing regimen for a plurality of dietary supplements to be administered to the subject to achieve the change from the initial nutritional condition toward the health condition.

The dietary supplement protocol server 128 can be configured for providing the protocol, regimen, and/or personalized dosage formulations to the user, such as to the mobile phone 140a (e.g., smart phone) or smart watch 140b. The user can then provide the protocol, regimen, and/or personalized dosage formulations to a dispenser 100 for formulating and dispensing the dosage formulations to the user. Alternatively, the dietary supplement protocol server 128 can be configured for providing the protocol, regimen, and/or personalized dosage formulations to the dispenser 100, and then the dispenser 100 can dispense the dosage formulations to the user.

The dispenser may also be configured with other components that are known in beverage dispensers, which components can be used for dispensing the personalized supplement dosage formulations. For example, the components recited in the incorporated references can be included in the present dispenser. Examples include: a formulation recipe database; a user preference database, interface module for a touchscreen; preference selection database; near field communication unit; biometric reader; biometric analysis unit; and others. The dispenser can include fluidic channels with one or more of: differential pressure sensor, pulse counter sensor, pumps, filtration system, sediment filter, water reservoir, cooling system, carbonating system, and the like.

In some embodiments, the dispenser is not a is not a 'beverage vending' system that dispenses a pre-determined and standard formula, recipe, beverage or the like to all users. Instead, the dispenser provides a formulation that is unique in the moment, for the user person in the particular environment.

In some embodiments, the supplement compositions in the cartridges can have viscosity in the range of 50 to 2000 cP.

In some embodiments, the system can include generating, at a controller associated with a micronutrient dispenser, a nutrition dose record and a performance history update record for a person that is formulated via a health and performance algorithm and dispensed at the micronutrient dispenser, where a variety of ingredients packages contain in liquid, gel, gaseous or powder form, ingredients and mixes of ingredients that can be added to any food or drink. This method may include writing dose and performance records to a database or data processing device associated with a cohort of individuals with similar or comparable health characteristics to those of the individual being dispensed, wherein the combined record is based at least in part on the dose and performance record of the individual being dispensed. The system can be configured for dynamically regulating and complementing a user's nutritional and health profile.

In some embodiments, the controller can include at least one non-transitory memory device storing computer-executable instructions; and at least one processor communicatively coupled to the at least one memory and the display and configured to access the at least one memory and execute the computer-executable instructions to implement the methods described herein.

In some embodiments, the system includes a health or nutritional supplement algorithm (e.g., in dispenser controller, server, or other) that produces the dosage formulation of the particular moment in time for the specific user. The formulation can be based on a history of the user's nutrition, habits, activity and performance, the sum of data of a cohort of similar individuals and their patterns of health/nutrition/supplementation practices. Also, the formulation can be based on health, nutritional, and other reference values including those related to maximizing bioavailability and doses throughout the day.

In some embodiments, micronutrient and supplements dispenser can include one or more of: a user interface operable to interact with a consumer and receive at least one input from the consumer (multiple health information parameters, performance, biometric, etc.); and a controller comprising a set of instructions operable to: receive, from an algorithmic dosing calculation system a dose combination of micronutrients and supplements with a variable formulation by time of day, moment in the life of the consumer.

The dietary supplement dispensers can be used in methods for providing customized and personalized dietary supplements to specific people. That is, a specific user can interact with the dispenser, such as having an account, where the dispenser determines the supplement dosage formulation that will be provided to the user during the interaction. The dispenser can obtain identification information from the user, and then acquire a dietary supplement protocol for the user. The dietary supplement protocol for that user may have a specific sequence of supplement dosage formulations that the immediate supplement dosage formulation can be selected from, or the protocol can be used for determining the immediate supplement dosage formulation based on health information of the user. The dispenser obtains the supplement dosage formulation parameters, and then determines the operation protocols of the dispenser for creating the supplement dosage formulation from water with one or more of the supplement compositions in the different cartridges. The water and one or more supplement compositions can be dispensed separately into the same container (e.g., glass, cup, bottle, etc.) for the user such that the formulation is created in the container.

Figure 7:
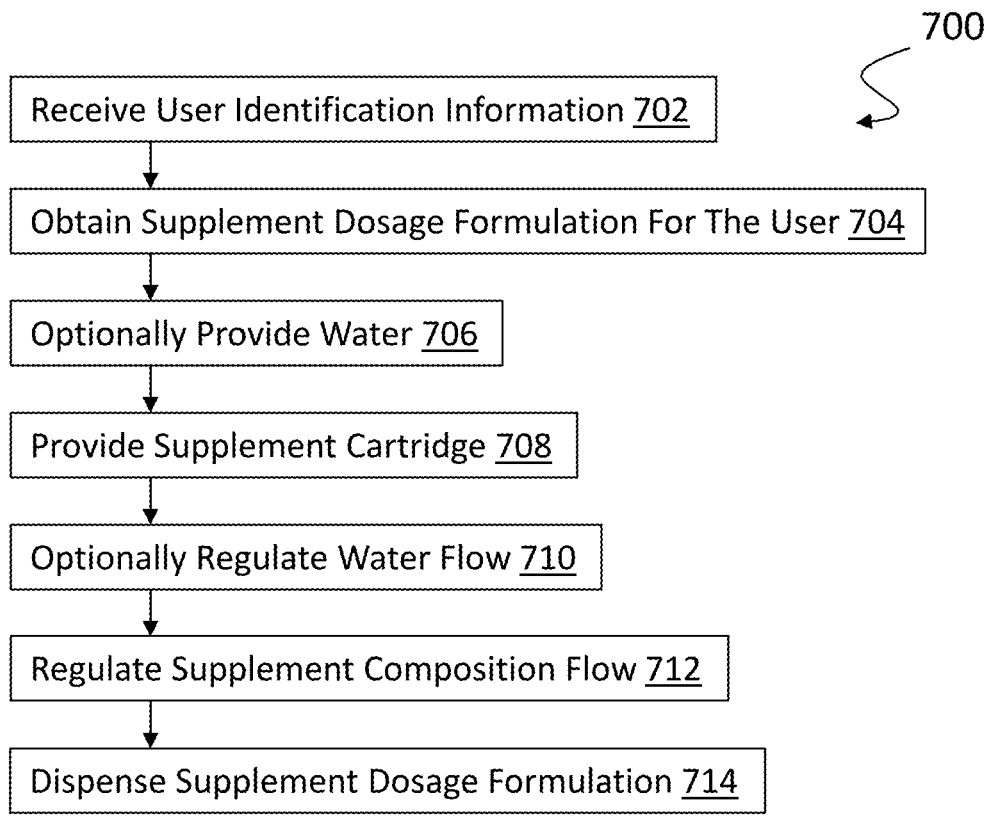
FIG. 7 shows a flowchart of a method of dispensing a supplement dosage formulation.

FIG. 7 illustrates a method 700 of providing a dietary supplement. The method 700 can include receiving identification information input from a user via the input device of the dispenser at block 702. Then, the method 700 can include obtaining a supplement dosage formulation for the user based on a dietary supplement protocol of the user at block 704. The method 700 can include optionally providing water for the supplement dosage formulation at block 706. The method 700 can include providing a plurality of supplement cartridges at block 708, wherein each supplement cartridge includes a supplement composition that is different from the other supplement compositions of the other cartridges. The method 700 includes optionally regulating fluid flow of the water to a water dispenser at block 710 (e.g., when water us used for dosage formulation). The method 700 includes regulating fluid flow of at least one supplement composition from at least one supplement cartridge to at least one supplement dispenser at block 712. Once the formulation is determined and the flow regulations are determined, then the method 700 includes controlled dispensing of the water and the at least one supplement composition of the plurality of supplement cartridges to provide the supplement dosage formulation to the user at block 714. The supplement dosage formulation that is provided can be a specific and personalized for the user for the particular time, day, or place as well as the parameters of the protocol.

The methods can also include determining a dietary supplement protocol as well as dosing regimens and specific formulations thereof. The protocol, regimens, and formulations can be determined by the controller of the dispenser, or the determinations can be made by a remote computing system. The determinations can utilize various information about the particular user, such as their identification information and health information. The protocol can also be used as a guide or model to determine the next dietary supplement formulation to be provided to the user, such as based on current needs or sequentially relevant formulations the user has received or will receive in the future in view of the overall protocol.

Figure 8:
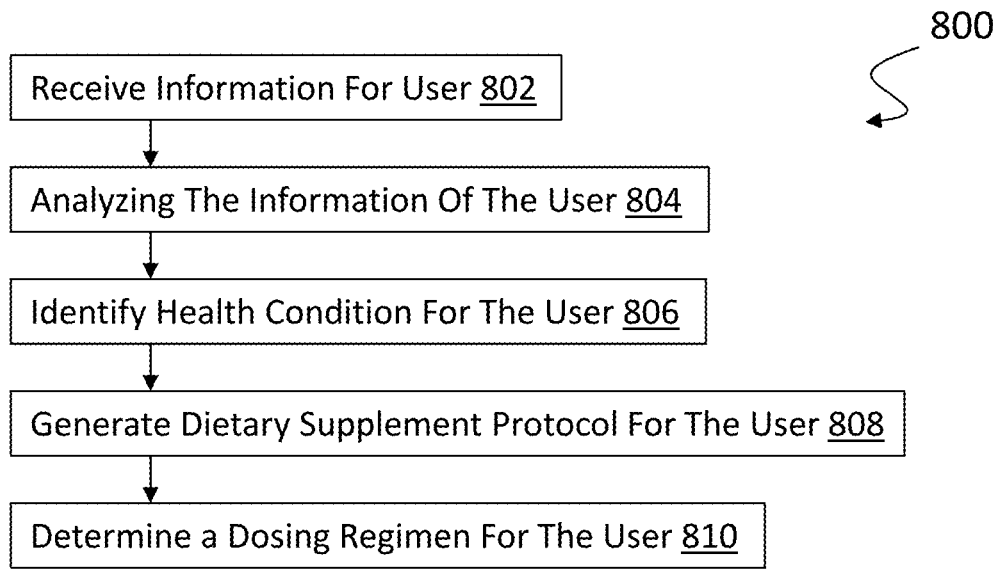
FIG. 8 shows a flowchart of a method of determining a dosing regimen for a user.

FIG. 8 illustrates a method 800 of determining a dosing regimen of dietary supplement formulations for a dietary supplement protocol. The method 800 can include receiving or otherwise inputting identification information and heath information for a user as input data into a computing system at block 802. Then, the method 800 can include analyzing the health information of the user by processing the identification information and heath information through a nutritional model to generate a nutritional condition for the user at block 804. The method 800 can include identifying a health condition in the nutritional model based on the nutritional condition of the user at block 806. The method 800 can include generating a dietary supplement protocol for the user to change an initial nutritional condition toward the health information improvement condition at block 808. Once the health information improvement is determined, then the method 800 can include determining a dosing regimen for a plurality of dietary supplements to be administered to the user to achieve the change from the initial nutritional condition toward the health information improvement condition at block 810.

The cartridges can be configured to include supplement compositions that contain vitamins and minerals that are used in numerous metabolic and chemical processes. The supplement compositions can be formulated with dietary supplements that can be used for helping the user with stress, disease, exercise, lack of sleep, ambient conditions, lack of nutrients and other factors that use vitamins and minerals in the users body. The supplement compositions can help the users' body balance physiological requirements through nourishment and can help accumulate reserves of some of these substances under many conditions.

However, it should be recognized that a user can have needs that fluctuate. The nutrition intake, ambient and activity conditions for the user can be fluctuated and can require constant attention. Food intake in normal conditions for most people requires some degree of supplementation that may not be optimally solved by the intake of large daily doses. Across a variety of vitamins and minerals the amount that can or is actually absorbed by the body varies from 10% to 90%, staying mostly well under 50%. Accordingly, the supplement compositions can be tailored and personalized for each dosage being consumed in order to alleviate any fluctuations. Each dosage can be formulated to alleviate a fluctuation in the users' needs, which can be to supplement food intake or lack of absorption of the supplements. The dosage formulation can be modified in real time to provide for increased absorption.

In some embodiments, the supplement compositions can be used for formulating personalized dosages for the user based on the user's health or health information. These personalized dosage can provide optimal bioavailability of nutrients, minerals and vitamins, which can be formulated in smaller doses, in balance with the levels of consumption imposed by stress, exercise, disease, available quality and varying nutritional intake, etc. For example, instead of one size fits all approximation of bodily requirements for nutrients, the dispenser can formulate the supplement compositions for a personalized dosage for a specific user. The dosing regimen can be configured with individual dosage formulations that are not too large, which allows for the supplements to be absorbed better instead of being lost through the digestive process and excreted, or otherwise not absorbed by the body. Thus, the dosing regimen with individual dosage formulations that are personalized can improve the uptake and health benefit of the supplements compared to bulk or generic dosing strategies for the masses.

In some embodiments, the dietary supplement protocol can be provided to a user through the digitally controlled dispensing of customized supplement dosage formulations, which are configured to include personalized individual doses of vitamins, minerals and nutrients per serving or per formulation. The personalization of each dosage formulation allows to more effectively supplement requirements for maintaining healthy body processes, ensuring the most bioavailable form of the formulated supplements. The dispenser controller or the server allows for the system to track the dosage formulations provided to the user over time. The health (e.g., health information) of the user is also tracked over the same time, which allows for a comparison on the change in health versus the dosage formulations that were provided. This provides a closed loop feedback mechanism to compare health data for a specific user over longer periods of use of the formulations. A large number of users can be served by a single dispenser or a single dispenser network (e.g., office having one or a plurality of separate dispensers) for diverse populations and large user groups, such as offices. For example, an office can have a dispenser system with a plurality of different dispensers, which allows a user to use any of the dispensers in the system to receive the dosage formulation.

The present invention provides for personalization of each dosage formulation for a user, which can be part of a dosing regimen of a dietary supplement protocol. For example, the supplement protocol can be generated or updated by obtaining information from each user regarding their physical traits as well as their activity and lifestyle. For example, every user can provide personal information input by answering questions about age, weight, height, level of activity, typical and preferred food and nutrition patterns, and also provide health information (e.g., inputs from wearable devices) such as heart rate variability, blood sugar, respiration, sleep patterns, and other health information. Any disease or disorder and state thereof can also be input. The input information allows the system to generate a dietary supplement protocol and offer supplementation in the dosage formulations that are personalized for each user at each instance of administration. This allows the dispenser to provide consumable solutions that have a dietary supplement profile that best corresponds with user defined goals or needs. For example, the goals of each user can be set in the system to support immunity, daily essentials, energy levels, and similar targeted outcomes.

The present invention provides for personalized formulations for each dose to achieve high bioavailability. The design of the cartridges in the system considers formulations and preparations that allow the dispenser to offer small and effective doses with minimal bodily process waste and minimal loss of nutrients through digestion or excretion. The supplement compositions in the cartridges use the most bioavailable chemical forms of the supplement substances. For many supplement substances there significant differences in how much the body can absorb, which is accounted for in each personalized dosage formulation. The supplement compositions in the cartridges use the most bioavailable preparation. The system works with liquid formulations that have been shown to allow the body a much higher absorption of some substances compared to solid pills and powders for example. The supplement compositions in the cartridges use special preparation forms, such as liposomes, which ensure direct absorption into the bloodstream through the intestinal tract and avoid the degradation during the digestive processes. The supplement composition can be configured to avoid the need to observe dietary requirements, such as taking liposoluble vitamins with fats during meals. The supplement compositions in the cartridges allow their combination in such way that ensures compatibility of the components and avoid overdosing some components that accumulate in the body. The supplement compositions allow the dosing in smaller quantities throughout the day. Supplementing in the right measure, in small doses, throughout the day, optimizes the bioavailability of nutrients and reduces the workload on the body to absorb what you ingest, to keep your metabolism working at its optimal level. Accordingly, a user can be scheduled to recommended to take at least one dose, such as two, three, or four or more dosages during the day, such as from the dispenser. The dosing regimen through the dispenser simplifies daily supplementation based on needs of the user to maintain optimal healthy conditions.

The supplement compositions can be designed to inhibit negative supplement interactions and/or promote positive supplement interactions with health. There are so many health aspects and nutrients users without the present invention would need considering for maintaining vital energy and a good health. Now, the present invention provides a system that assists people who are not willing to keep track of the many supplement interactions. The system can also inform personal health coaches and doctors allowing them to offer better advice to their clients. For example, an office having at least one dispenser allows the employer to provide personalized dosage formulations that are important to support immune health levels, energy and attention levels in work groups.

The supplement can include the following substances that can have interactions: Vitamin D intake effects on the immune system, bone health, hormone production and nervous system; Omega-3 effects on reducing body inflammatory processes and brain function; Vitamin B complex effects on the function of neurotransmitters, coenzymes in fat and carbohydrate metabolism; Magnesium effects in over 600 studied enzymatic metabolic reactions in the body; Selenium and Zinc functions in preventing cellular damage from free radicals. Thus, the supplements can help interrelated processes for example between gut-health and immunity The supplement compositions can include a beneficial complementarity of herbal and other natural products. While the health claims of herbals are not always demonstrated to the same standards of vitamins and minerals, they are widely regarded as offering benefits and causing no harm. The system allows the user to incorporate supporting cartridges that may offer such complementary benefits for example for immunity and reduced inflammation levels in joints, to support the gut microbiome—the seat of our immunity.

The dispenser system is configured to monitor and track hydration for each user. The system supports and tracks the consumption of the supplements with water, therefore supporting information about the consumption of water which in itself is useful for the consumer. Thy hydration information can be health data that is used to generate or modify a dietary supplement protocol.

In some embodiments, the dispenser system can provide a multi-month program for each user that is personalized with a unique dosage formulation for each user at each administration. For example, bringing the immune system of a user to a steady low maintenance level requires supplementation for a period of time, such as through a regimen. For example, immune system cells, blood cells performing a variety of immune system functions, require 3-4 months to renew. Stores of Zinc and Vitamin D, may take 1-2 months to recover high healthy levels when they are very low in a user.

In some embodiments, the dispenser system includes concentrated supplement formulations that have diverse types of supplements in combination. The supplements can include vitamins, minerals, fatty acids, antioxidants, phytonutrients, amino acids, and other nutrients carefully selected in their optimum chemical form for better bioavailability. These cartridges can include concentrated supplement formulations that are subject to personalized dosing based on each user's body, and optionally based on ambient parameters and changing daily factors in activity (under- and over exercise, mental activity), diet, rest (e.g., health information input). The dispenser system offers the user the ability to distribute smaller doses throughout the day or take all doses at once if the schedule or preferences require it, which can be performed by adjusting the amounts of supplement composition that is dispensed in each dosage formulation.

In one embodiment, the different cartridges of a dispenser system can be defined to support a well-functioning immune system with the following mixes of vitamins, minerals, fatty acids, antioxidants, phytonutrients, amino acids, and other nutrients. An example includes: Daily multivitamins and minerals (cartridge 1); Immunity boost (cartridge 2); Fat soluble (cartridge 3); and Healthy gut (cartridge 6). These different cartridge compositions are mixed and served through a regimen or supplement protocol, such as for a month long program. In another example, a performance and energy enhancing program uses a different mix focusing on the following body systems: Electrolytes (Cartridge 4); Energy enhancement (cartridge 5); and Healthy gut (cartridge 6). A significant number of bodily systems and functions can be addressed by similar programs adding a diversity of cartridges including but not limited to: Nervous system and brain function; Organ support; Heart health; Bones and joints; and Skin.

In some embodiments, a supplement composition can be configured as a daily essentials composition with vitamins and minerals. Such a daily essentials composition contains vitamins and certain minerals that are essential for everyday metabolism. The quantities are small but they are indispensable compounds, which aid in the utilization of food people consume. These compounds assist thousands of enzymes, which need vitamins and minerals for their synthesis or as cofactors in order to catalyze vital metabolic processes in human bodies. The quantities are defined in such a way that doses from this cartridge can be dispensed alone or in combinations with other cartridges. In an example, daily essentials include: B vitamins, vitamin C, folate, magnesium, selenium, zinc, iron, iodine and others. vitamin C contributes to collagen formation for the normal function of blood vessels, bones, cartilage, gums, skin and teeth. Vitamin B12, vitamin B6 and folate contribute to normal homocysteine metabolism and to normal red blood cell formation. Folate and vitamin B12 have a role in the process of cell division. Vitamin B6 contributes to the regulation of hormonal activity.

In some embodiments, a supplement composition can be configured as an immunity boosting composition. Immunity is affected by stress, insufficient and excessive exercising, unbalanced diet, gut microbiome, poor sleep, general vitamin deficit, stimulants (e.g., coffee), alcohol, chronic disease, and inflammation. An immunity boosting composition includes nutrients needed for boosting immunity so that the body can function at its optimum on a daily basis, prevent disease and to resist viral and bacterial infections. Nutrients supporting immunity include: vitamin C, vitamin D3, zinc, selenium, B vitamins, omega-3 fatty acids and others. Vitamin C contributes to maintain the normal function of the immune system, to the protection of cells from oxidative stress, contributes to energy-yielding metabolism, reduction of tiredness and fatigue and functioning of the nervous system. Vitamin B12 and Vitamin B6 contribute to the normal function of the immune system.

Vitamin D contributes to the normal function of the immune system. Vitamin D has a role in the process of cell division. Vitamin D contributes to normal absorption/utilization of calcium and phosphorus, maintenance of normal bones and teeth and normal muscle function. Vitamin A contributes to the normal function of the immune system, maintenance of normal mucous membranes, skin and vision. Vitamin A has a role in the process of cell specialization.

Vitamin E contributes to the protection of cells from oxidative stress. Vitamin K contributes to normal blood clotting and to the maintenance of normal bones. DHA and EPA contribute to the normal function of the heart, to the maintenance of normal blood triglyceride levels and normal blood pressure. Coenzyme Q10 (CoQ10) is an antioxidant that our body produces naturally. Cells need CoQ10 for growth and maintenance.

In some embodiments, a supplement composition can be configured as an energy boosting composition. The fundamental source of energy in all body processes comes from special structures present in every human cell called mitochondria. Rather than relying on stimulants like caffeine the cartridge relies on micronutrients that support mitochondrial functioning. Disfunction at this level manifests through fatigue, brain fog, anxiety and depression, loss of resilience and altered sleep patterns. Mitochondria work in defense mode or energy-building mode. They cannot do both at a time. Hence a good level of supplementation aids in maintaining higher energy levels. All B vitamins contribute to normal energy-yielding metabolism. Vitamin B6, folate, vitamin B12, vitamin B2 (riboflavin), vitamin B3 (niacin), vitamin B5 (pantothenic acid) contribute to the normal functioning of the nervous system and to the reduction of tiredness and fatigue. Vitamin B1 (thiamine) contributes to normal functioning of the nervous system and to the normal function of the heart. Vitamin B2 (riboflavin) contributes to the maintenance of normal red blood cells, normal mucous membranes, skin and vision. Vitamin B2 (riboflavin) contributes to the protection of cells from oxidative stress and to the normal metabolism of iron. Vitamin B7 (biotin) contribute to the maintenance of normal mucous membranes. Vitamin B5 (pantothenic acid) contributes to normal mental performance, to normal synthesis and metabolism of steroid hormones, vitamin D and some neurotransmitters.

In some embodiments, a supplement composition can be configured as a supplement solubilizing composition. Fat soluble vitamins accumulate in the body and offer higher risks of overdosing. Intake in most forms is recommended with foods and fat intake, but in certain forms like liposomes, smaller doses can be very effectively absorbed directly in the bloodstream through the small intestine membrane. Some examples can include Vitamin D3 (cholecalciferol) and vitamin K2 (menaquinone) and omega-3 fatty acids (EPA, DHA) and coenzyme CoQ-10. For better bioavailability, these vitamins are formulated in liposomal form.

In an example, a morning formulation can include 300 ml of water and a dose of daily essentials. Then, a midday formulation can include 300 ml of water with vitamin D3, vitamin K2, and omega-3. An evening formulation can include a formulation for a sports bottle, which can include an immunity boost composition (e.g., cart. 2) and/or an energy boost composition (e.g., cart. 5).

Table 1 provides an example of cartridge compositions.

TABLE 1

| Element | units | Cart 1 Daily essentials | Cart 2 Immunity | Cart 3 Fat solubles | Cart 4 Electrolytes | Cart 5 Energy boost | Cart 6 Gut Health |
|---|---|---|---|---|---|---|---|
| C | mg | 200 | 800 | | | | |
| B12 | mcg | 100 | 100 | | | | |
| B9 Folate | mcg | 400 | 0 | | | | |
| B6 (Pyridoxine) | mg | 50 | 0 | | | 75 | |
| Mg (Malate) | mg | 200 | 0 | | | 30 | 200 |
| Se (selenomethionine) | mcg | 55 | 45 | | | 45 | |
| Zn (Orotate, Picolinate) | mg | 10 | 20 | | | 20 | |
| K (Citrate, Chloride) | mg | 50 | 0 | | | 50 | |
| Ca (Citrate) | mg | 200 | 0 | | 30 | | |
| Fe (Succinate) | mg | 10 | 0 | | | | |
| Cu (Gluconate) | mg | 1 | 1.5 | | | | |
| I (Potassium Iodite) | mcg | 100 | 50 | | | 50 | |
| Choline (Phosphatidylcholine) | mg | 100 | 0 | | | | 400 |
| Cr (Picolinate) | mcg | 35 | | | | | |
| D3 (Cholecalciferol) | mcg | | | 100 | | | |
| K2 (Menaquinone-7) | mcg | | | 40 | | | |
| A (Palmitate) | mcg | | | 900 | | | |
| E (d-alpha tocopherol) | mg | | | 15 | | | |
| Omega-3 | mg | | | 200 | | | |
| Ubiquinel | mg | | | 50 | | | |
| Na (from sodium chloride) | mg | | | | 80 | | |
| Cl (sodium and potassium) | mg | | | | 80 | | |
| P | mg | | | | 30 | | |
| B3 Niacin | mg | | | | | 25 | |
| B1 thiamine | mg | | | | | 5 | 5 |
| B2 riboflavin | mg | | | | | 5 | |
| B8 (Inositol NF) | mg | | | | | 100 | 500 |
| B5 Panthothenic Acid/Calcium pantothenate | mg | | | | | 5 | |
| B7 (Biotin, Vit H) | mcg | | | | | 300 | |
| L-Carnitine | mg | | 0 | | 350 | 250 | 500 |
| N-Acetylcysteine | mg | | | | | 500 | |
| Methyl-Sulfonyl-Methane (MSM) | mg | | | | | 1000 | |

The dietary supplement protocol can be implemented with the dispensers described herein or other modes of administration. The dietary supplement protocol can be offered as a wellness program from any type of environment, such as a school, workplace, gym, home, or the like. For example, the dietary supplement protocol can be implemented in a wellness program at a place of employment, which can provide the personalized smart hydration and supplementation to provide positive health benefits and reduce health risks. The programs can be implemented to help employees improve health behavior. The program can also include instructions or operations to help people change their diets and make exercise a habit. In some aspects, the program or protocol can last 30, 60, 90, or 120 days.

In some embodiments, the system can include an application that operates on a device (e.g., 140a, 140b) of the user. The application can be configured to acquire personal information and health information from the user and provide it to the system for use in creating or updating the protocol. The application can be configured to interact with the dispenser so that the user is identified and the dispenser formulates the correct dosage formulation for the specific user at the time the formulation is being dispensed. The application can also receive data from the system, and can provide data to the user. For example, the application can be used to schedule the daily dosages of the protocol. The application can also provide alerts and notifications to the user regarding dosages. The application can also provide for data ascertainment regarding the daily activities, health, or other aspect of the user that can be used for generating or modifying a dietary supplement protocol. In some embodiments, the application can be used for tracking hydration and supplementation, which may also be tracked by the dispenser controller or the system server. This can allow for the system to provide feedback regarding the health condition to the user. In an example, the application can be used for obtaining information about the user body parameters and daily routines (e.g., exercise and diet), and providing a supplementation plan to the user. The application can track performance and activity of the user and can correlate dosage formulations to changes in performance and activity. The application can be used to input biometrics for the user, which can be used for providing a more robust and personalized protocol. The application can also be used to transfer the personal information, health information, or dietary supplement protocol to a doctor or other care giver or health coach for the user. However, these actions can be performed by the dispenser controller or the system server.

In some embodiments, the protocols can be generated or modified by obtaining updated health information. The user can get their biological samples (e.g., blood, urine, etc.) analyzed, and then provide the health information for use in tracking the user and modifying the protocol and formulations. The health information can include: complete blood count (CBC) plus ESR; lymphocyte subpopulation tests; total antibodies—IgG, IgA, IgM; C reactive protein (CRP-hs); levels of cytokines (interleukin—6 and others); homocysteine; vitamin D; omega-3/omega—6 ratio; antioxidant mini profile; heart rate variability (HRV); biomarker analysis; or others.

In some embodiments, the dosage forms each include a temporally-personalized dosage that is formulated with a combination of the plurality of dietary supplements to provide the subject with a personalized dietary supplement regimen that dynamically personalizes delivery of each dietary supplement in each temporally-personalized dosage in accordance with the dietary supplement protocol.

In some embodiments, the methods include providing the subject with instructions for administration of the dosage formulations to the subject in accordance with the updated dosing regimen to perform the dietary supplement protocol.

In some embodiments, the system provides instructions for the dosage formulations to the user. The user can then prepare the formulations based on the instructions. For example, the user can have one or more cartridges or containers with the different supplement compositions, and the user can then prepare each formulation based on directions or recipe provided to the user. In some instance, the formulation is provided to the dispenser, and the dispenser provides the formulation to the user. In any event, the dietary supplement protocol and individual dosage formulations can be provided by the system as instructions or other data for preparation of the dosage formulations by the user or a dispenser.

In some embodiments, the health information includes disease states, energy level, activity level, stress level, typical diet, amount of rest or sleep, any drinking of alcohol, any consumption of drugs, any smoking, pregnancy, menopause, age-related conditions, or others. The health information may also be related to the environmental conditions that the subject experiences, such as weather, pollution, pollen, ambient conditions, or the like. The identification and health information can be processed through a model or algorithm or other computation to generate a supplement protocol that is personalized for each user. The supplement protocol can be an overall plan for increasing the health or performance of the user toward an improved condition. The supplement protocol can include a regimen of one or more dosages of personalized formulations that can help the user improve their health and performance.

The personalized dosage formulations can be provided to the user for direct consumption, or the formulations can be provided as instructions for preparation provided to a dispenser that dispenses. The personalized supplement program can include a dietary supplement protocol that includes one or more supplement dosing regimens, which further includes a plurality of individual dosage formulations. Each dosage formulation is personalized for the specific user. The personalization can be from user preference for dietary supplement and health goals. The personalization can also be from the user providing identification information and health information, which is then processed to determine the dietary supplement protocol, dosing regimens, and individual personalized dosage formulations. The user can fill out a questionnaire to provide information regarding health information, such as weight, height, age, gender, level of activity, typical diet, and the like. The health information may also be obtained passively or actively from a device of the subject or other device, such as a scale, an electronic reading of data, or an application on a smart phone. The health information may also be based on invasively obtained data from analysis of a sample from the subject. This information can be matched with their identification information (e.g., name, security number, login, etc.).

The dosage formulation may or may not include water added to a supplement composition. The supplement compositions can be provided alone or in combination or with or without water for preparing the dosage formulation. The dosage formulation can be added to any type of consumable, from solid foods to liquid beverages and anything else that is consumable.

In some embodiments, the input data for the subject in any of the methods can be by passive input methods. That is, the data can be collected and automatically provided to the system for us in generating the protocols or the relevant dosing formulations. Some examples of passive methods to the input and/or reading of the health condition can include: capture the height, weight, heart rate or other health indicator automatically by a supplement dispenser, such as the dispenser identifying the subject approaching the machine or after interacting with a device, such as having a picture taken stepping on a scale; or invasive methods that take a sample from the subject. The invasive methods can biometric monitoring with those techniques listed herein as well as invasive technologies, such as any blood metrics and blood analysis means, which can include blood glucose (e.g., Continuous Glucose Meter (CGM)) as well as meters for other molecules (e.g., lactate, ketones, etc.) that use a biological sample. For example, the invasive technologies can include obtaining dialysis blood measurements to help a subject to supplement their outcomes, such as determining the subject to be low on electrolytes.

In some embodiments, the dosage formulation includes any type of dietary supplement in a suitable dosage. In some aspect, the suitable dosage is a micro-dosage, which is sometimes referred to as micronutrients. Now, a regimen, such as daily or weekly, etc., can be prepared to include the dosage formulations having the nutrients in micro-dosages to provide micronutrients. For example, a daily regimen can include a plurality of dosages each having micronutrients that are best absorbed/bioavailable in the body in smaller more frequent doses, such as vitamin C, B complex and other water soluble or lipid soluble substances. The formulations can include micronutrients such as vitamins, minerals, enzymes, botanicals, herbs, or other dietary supplements that may be essential for enzymatic processes, biochemical processes or any other biological pathway in the fine machinery of the body (e.g., cell reproduction, energy in the cell) which is affected by hourly, daily, weekly fluctuations.

In some embodiments, the dietary supplement protocol can be determined based on the health information of the subject. The health information can generally be related to the overall health of the subject regarding their disease states, biological function, activity information, and other information that contributes to the health of a person, such as environment information, and life habit information as well as other information indicative of health.

In some embodiments, the dietary supplement protocol is configured with the dosage formulations to improve the health of the subject, which includes improving the indications related to overall health of the subject regarding their disease states, biological function, activity information, and other information that contributes to the health of a person. This may also include improving activity and life habits. In addition to improving health, the dietary supplement protocol and the dosage formulations can be configured to maintain homeostasis in the subject in one or more areas, such as those recited herein. The maintaining of homeostasis allows for the steady functioning of one or more health indicators or biological processes over a period of time or through at least one stimulus or stressful condition. That is, the dosage formulations in a regimen can be configured for homeostasis when the subject experiences a negative stimulus, such as oxidative processes typical of infection, disease, stress, exertion, as well as free radicals also triggered by pollution, allergies, weather (environmental) or the like.

In some embodiments, the nutritional condition of the subject can be related to the nutrients for health in relation to activity, stress, diet and life habits (e.g., drinking, smoking, resting, exercising, eating, etc.). The nutritional condition is an indication of the nutritional state of the subject as it relates more broadly to maintain the good functioning of body processes (e.g., homeostasis) or improving functioning of the body processes. the model can provide the nutritional condition, which is a nutritional snapshot of the health condition of the subject.

In some embodiments, the dietary supplement protocol can include providing dietary supplements to modulate biological processes for obtaining the target health condition (e.g., the health condition identified in the nutritional model based on the nutritional condition of the subject). In an example, in some cases, such as blood glucose, the target may be to reduce glucose spikes. For example, before lunch the dosage formulations can be configured to include a supplement that dampens glucose spikes for this particular subject. The system could learn over time that on certain days the subject eats more carbs/sugars than on other days, and then the system proactively doses supplements to minimize the impact of the carbs/sugars. Alternatively, the system can be configured to read the meal information that is being served to the subject from an external menu (e.g., Playground publishes the lunch menu that is obtained by the system) and then the system prepares the appropriate dosage formulation to include the proper amount of the supplement to counteract the consequences of the meal (e.g., lunch).

In some embodiments, the health condition that is identified can be an improvement condition or maintaining a condition of the subject. This allows the health condition to be a goal to be achieved in the subject by using the dosage formulations of the dietary supplement protocol. This allows the goal of the protocol to be identified, and then the dosage formulations are prepare to meet this goal. In some instance, the subject identifies some goals for a health condition by providing goal input information. In some instances, the system identifies goals for a health condition, which can be based on the identification information and health information as well as the other related information described herein, such as activity, lifestyle, environment, and the like.

In some embodiments, the goal of the health condition can be personalized for a goal specific to the subject without consideration of the population at large. That is, the goal is tailored to improve the subject specifically for something the subject needs, such as more activity, more energy, or more sleep, as well as others. In other embodiments, the goal of the health condition can be personalized in relation to the population at large. That is, the goal is tailored to improve the subject in relation to standards or averages of a given population, such as people in a geographic region, a specific gender, an age range, or others as well as combinations. Some examples of the goals can include: the same or more activity, the same or more energy, or the same or more sleep, the same or more immunity, improve a temporal imbalance, reduce stress, reduce effects of a disease state, and reduce infections, as well as others. Accordingly, the health condition to be achieved in the subject can include population goals, such as being based on a blood test, and the system determines a subject having vitamin D that is below the population average. The health condition to be achieved in the subject can include individual goals, such as subject wanting more energy or to improve sleep.

In some embodiments, the health condition includes a goal to provide improvement to the subject in at least one biologically-relevant area. The improvement can be understood as reducing a gap between a current state and a desired state. For example, the goal can be to improve immunity, overcome temporal imbalances, and improve a response in the subject after a stressful activity, a disease, or an infection, as well as others.

In some embodiments, the generated dietary supplement protocol can be generated at the request of a consumer, doctor, trainer, dietician, or any other third party. In some embodiments, the generated dietary supplement protocol can be approved or selected by the consumer, doctor, trainer, dietician, or any other third party.

In some embodiments, subjects that have a specific biomarker or other indication may be more at risk of a certain disease state, and the subject may be prescribed or recommended to take a specific supplement to help reduce the risk. Accordingly, the methods described herein can also include: performing credible research on the disease state; based on the analyses described herein, recommending a supplement or supplement combination (e.g., dosing formulation) as part of the regimen and protocol; obtaining approval thereof from the consumer, doctor or other third party; and add the supplement or supplement combination to the subject's regimen. As research is updated and more is known, the system (e.g., by the server) can remotely update the formulations and recommendations provided to the user's device or to the dispenser system.

In some embodiments, the personalized dietary supplement regimen dynamically personalizes delivery of each dietary supplement in each temporally-personalized dosage in accordance with the dietary supplement protocol.

In some embodiments, the health condition is at least one of: a health condition improvement compared to an initial health condition of the subject; maintaining a health condition to be about the same as an initial health condition of the subject; an increase in energy for the subject; maintaining an energy level for the subject; an increase in activity for the subject; maintaining an activity level for the subject; increasing activity of a biological pathway in the subject; maintaining activity of a biological pathway in the subject; reducing activity of a biological pathway in the subject; increasing immunity of the subject; or maintaining immunity of the subject.

In some embodiments, the methods can include at least one of: providing information to the subject about their daily habits; providing recommendations to the subject about changing their daily habits; or personalizing the dosage formulations for the subject based on their daily habits.

In some embodiments, the health condition is a goal for the subject to achieve with the dosage formulations, wherein the goal is selected from: the same or more activity, the same or more energy, or the same or more sleep, the same or more immunity, improve a temporal imbalance, reduce stress, reduce effects of a disease state, and reduce infections, or combinations thereof. In some aspects, the health condition to be achieved in the subject includes population goals or individual goals. In some aspects, the goals are related to achieving a similar benchmark or an improvement in heath condition biomarkers, such as heart rate variability, blood pressure, pulse, recovery rates, breathing, quality of sleep/deep sleep, blood test indicators such as Vitamin D.

In some embodiments, the methods include: tracking an amount of each dietary supplement in each dosage formulation for a subject; and saving or reporting to the subject the tracked amount of each dietary supplement for each dosage formulation or over a plurality of the dosage formulations.

In some embodiments, the process of identifying the subject is by at least one of: input into a device from the subject or a different person; active data from a device of the subject; passive data from a device of the subject; a signal from a device in response to a probe signal from a dosage dispenser; or passive or active acquisition of data of the subject by a dosage dispenser.

The embodiments are forth in the independent claims herein. However, it should be recognized that any dependent claim from any independent claim may also depend from any other independent claim. That is, the subject matter of the dependent claims can be used with any of the methods of the independent claims or any other methods described herein.

One skilled in the art will appreciate that, for the processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

Figure 6:
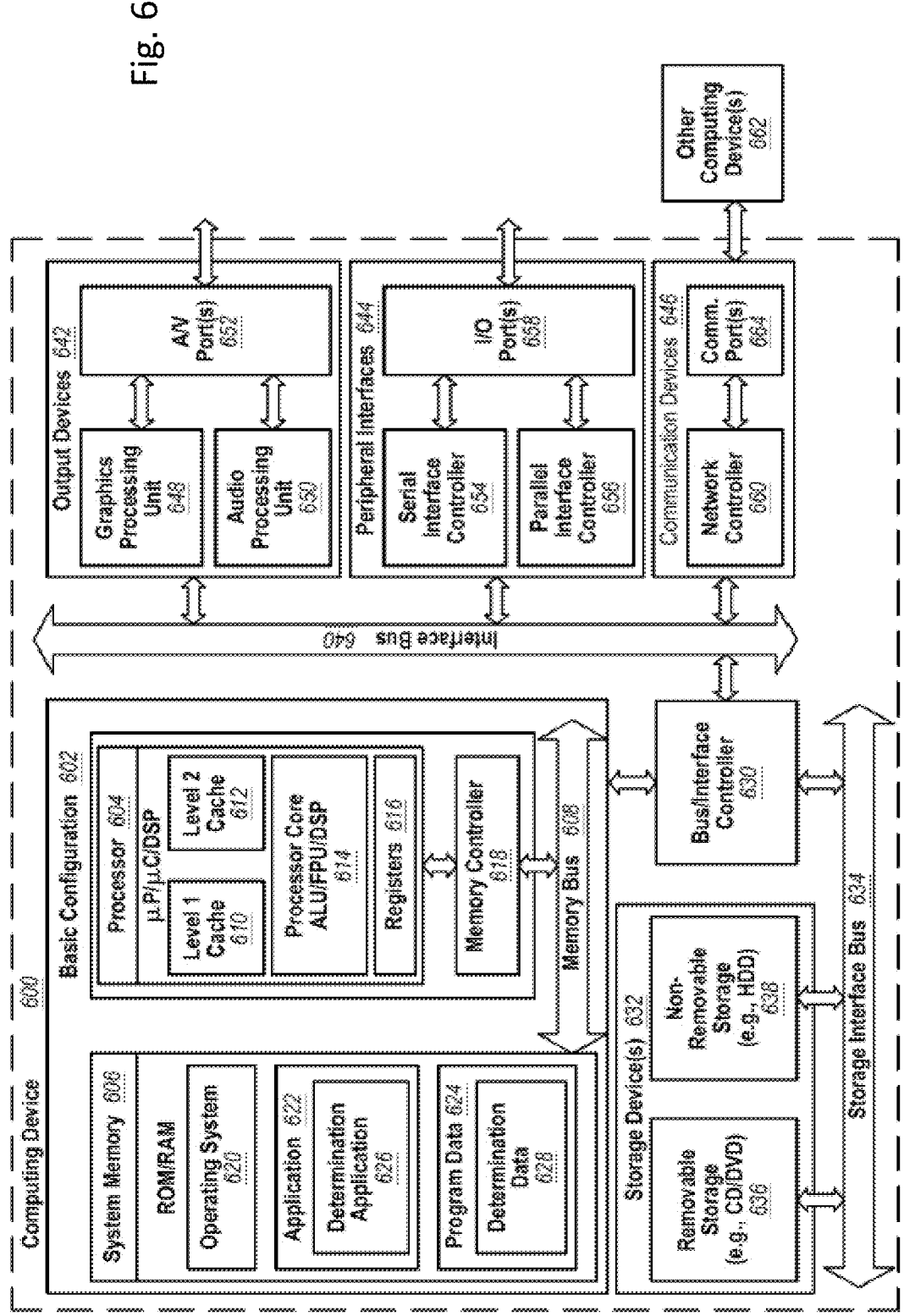
FIG. 6 shows an example computing device (e.g., a computer) that may be used as a dispenser controller to perform the methods (or portions thereof) described herein.

FIG. 6 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor (µP), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In some embodiments, a computer program product can include a non-transient, tangible memory device having computer-executable instructions that when executed by a processor, cause performance of a method that can include: providing a dataset having object data for an object and condition data for a condition; processing the object data of the dataset to obtain latent object data and latent object-condition data with an object encoder; processing the condition data of the dataset to obtain latent condition data and latent condition-object data with a condition encoder; processing the latent object data and the latent object-condition data to obtain generated object data with an object decoder; processing the latent condition data and latent condition-object data to obtain generated condition data with a condition decoder; comparing the latent object-condition data to the latent-condition data to determine a difference; processing the latent object data and latent condition data and one of the latent object-condition data or latent condition-object data with a discriminator to obtain a discriminator value; selecting a selected object from the generated object data based on the generated object data, generated condition data, and the difference between the latent object-condition data and latent condition-object data; and providing the selected object in a report with a recommendation for validation of a physical form of the object. The non-transient, tangible memory device may also have other executable instructions for any of the methods or method steps described herein. Also, the instructions may be instructions to perform a non-computing task, such as synthesis of a molecule and or an experimental protocol for validating the molecule. Other executable instructions may also be provided.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety. This application cross-references co-pending U.S. application Ser. No. 17/117,871, Dec. 10, 2020 and entitled "PERSONALIZED DIETARY SUPPLEMENT PROTOCOL AND DOSAGE FORMULATIONS."

References: U.S. Pat. Nos. 3,572,553; 1,591,799; 3,250,433; 6,223,944; WO 2001079072; U.S. Pat. Nos. 9,790,079; 4,595,131; 6,196,420; 3,218,175; 3,848,776; 6,557,735; US 2005/0092769; U.S. Pat. Nos. 4,755,292; 3,060,703; 7,861,646; 6,073,539; US 2006/0000851; U.S. Pat. Nos. 5,114,047; 5,312,017; 10,464,797; 7,028,603; US 2009/0064866; U.S. Pat. Nos. 7,669,738; 9,212,041; 9,646,314; 5,390,826; US 2014/0239013; US 2006/0115570; EP 2733122; U.S. Pat. Nos. 9,668,508; 10,723,541; 10,279,985; 9,932,217; 10,231,567; 10,765,252; US 2013/0092567; U.S. Pat. Nos. 10,674,857; 8,768,524; 9,773,265; 9,051,162; 10,017,372; 10,059,581; US 2017/0099981; U.S. Pat. Nos. 7,806,294; 9,622,615; US 2006/0118581; U.S. Pat. Nos. 5,540,355; 4,958,747; 4,030,634; 5,256,279; 5,531,908; 6,793,099; 6,453,955; 6,382,467; CA 2124681; U.S. Pat. Nos. 3,363,807; and 8,728,535; US 2015/0105880; U.S. Pat. No. 8,170,405; CN 101346288; RU 2487415; U.S. Pat. No. 4,015,755; IE 47040; U.S. Pat. No. 10,694,655; US 2010/0146587; U.S. Pat. Nos. 8,309,030; 7,762,181; US 2019/0084757; U.S. Pat. Nos. 9,533,867; 10,435,285; 9,679,329; 7,438,941; and U.S. Pat. No. 8,606,379.

The invention claimed is:

1. A dietary supplement dispenser comprising:
   a plurality of supplement cartridges, each supplement cartridge including a supplement composition that is different from the other supplement compositions of the other cartridges;
   at least one dispenser fluidly coupled with the plurality of supplement cartridges;
   an input device configured to receive input regarding a user;
   a dispenser controller operably coupled with the plurality of supplement cartridges and input device, wherein the dispenser controller is configured to:
      receive identification information input regarding the user via the input device;
      obtain a supplement dosage formulation for the user based on a dietary supplement protocol of the user; and
      control dispensing of at least one supplement composition of the plurality of supplement cartridges to provide the supplement dosage formulation to the user; and
   at least one supplement meter operably coupled with a reservoir having the supplement composition of each supplement cartridge, wherein the dispenser controller is configured for monitoring supplement usage by at least one user with the at least one supplement meter and tracking supplement usage for the at least one user over a time period for each supplement composition.

2. A dispenser system comprising:
the dispenser of claim 1; and
a mobile device having a non-transitory memory device containing executable instructions for operating an application that interacts with the dispenser to obtain data from the user and/or to provide information to the user.

3. The dispenser of claim 1, further comprising a water source inlet configured for receiving water, and wherein the controller is configured to control dispensing of water with or without dispensing the at least one supplement composition.

4. The dispenser of claim 1, further comprising a UV-C light configured for irradiating the water upstream of the at least one dispenser.

5. The dispenser of claim 1, further comprising a water meter operably coupled with a water source inlet, wherein the dispenser controller is configured for controlling water dispensing and monitoring water usage by at least one user and tracking water usage for the at least one user over a time period with the water meter.

6. The dispenser of claim 1, further comprising a transceiver operably coupled with the dispenser controller and configured to communicate over a network to transmit identification information for at least one user to a dietary supplement protocol server and configured to receive the supplement dosage formulation of a dietary supplement protocol for the at least one user from the dietary supplement protocol server.

7. The dispenser of claim 1, further comprising a port for each supplement cartridge, wherein each port is configured for removably receiving the respective supplement cartridge therein and fluidly coupling with the supplement composition.

8. The dispenser of claim 1, wherein the at last one dispenser includes at least one nozzle configured as at least one of: a water only nozzle operably coupled with a water source inlet, a supplement only nozzle for at least one supplement composition, a supplement only nozzle for each supplement composition, and a water and supplement combination nozzle.

9. The dispenser of claim 1, further comprising a formulation mechanism operably coupled with the plurality of supplement cartridges, wherein the formulation mechanism is configured for regulating fluid flow from the plurality of supplement cartridges to the at least one dispenser, wherein the formulation mechanism includes at least one: flow regulator; flow channel; pump; cartridge pump for each supplemental cartridge; mixer; heater; valve; cooler; water from the water source; supplement composition from the at least one cartridge; and/or dosage formulation as a mixture from the water and at least one supplement composition.

10. The dispenser of claim 1, wherein the input device is configured to receive a signal from a device of the user, wherein the signal can be a signal from a mobile device, WiFi module, Bluetooth module, RFID tag, near field communication tag, or other signal provider designated to the user.

11. The dispenser of claim 1, wherein the input device is configured to receive manual data input from the user, wherein the input device includes a touch screen, display, keyboard, mouse, microphone, camera, or combination thereof.

12. The dispenser of claim 1, further comprising at least one water filter fluidly coupled with a water source inlet upstream of a formulation mechanism.

13. The dispenser of claim 1, wherein a water source inlet is configured to be fluidly coupled with a water source selected from the group consisting of: a water container; a water line; a water dispenser; a water cooler; a water heater; a filtration unit; and combinations thereof.

14. A method of providing a dietary supplement comprising:
providing the dietary supplement dispenser of claim 1;
receiving identification information input from a user via the input device;
obtaining a supplement dosage formulation for the user based on a dietary supplement protocol of the user;
providing a plurality of supplement cartridges, each supplement cartridge including a supplement composition that is different from the other supplement compositions of the other cartridges;
regulating fluid flow of at least one supplement composition from at least one supplement cartridge to at least one supplement dispenser; and
controlled dispensing of the at least one supplement composition of the plurality of supplement cartridges to provide the supplement dosage formulation to the user.

15. The method of claim 14, further comprising:
inputting identification information and heath information for the user as input data into a computing system;
analyzing the health information of the subject by processing the identification information and heath information through a nutritional model to generate a nutritional condition for the user;
identifying a health information improvement condition in the nutritional model based on the nutritional condition of the user;
generating a dietary supplement protocol for the user to change an initial nutritional condition toward the health information improvement condition; and
determining a dosing regimen for a plurality of dietary supplements to be administered to the user to achieve the change from the initial nutritional condition toward the health information improvement condition.

16. The method of claim 14, further comprising regulating water flow in the dispenser.

17. The method of claim 16, further comprising regulating dispensing of water to provide the supplement dosage formulation.

18. A dietary supplement dispenser comprising:
a plurality of supplement cartridges, each supplement cartridge including a supplement composition that is different from the other supplement compositions of the other cartridges;
at least one dispenser fluidly coupled with the plurality of supplement cartridges;
an input device configured to receive input regarding a user;
a dispenser controller operably coupled with the plurality of supplement cartridges and input device, wherein the dispenser controller is configured to:
receive identification information input regarding the user via the input device;
obtain a supplement dosage formulation for the user based on a dietary supplement protocol of the user; and
control dispensing of at least one supplement composition of the plurality of supplement cartridges to provide the supplement dosage formulation to the user; and a formulation mechanism comprising:
at least one pump operably coupled with a water source inlet and a water dispenser of the at least one dispenser;
a cartridge pump coupled to each supplement cartridge and a supplement dispenser of the at least one dispenser;
at least one water flow channel; and
a plurality of supplement cartridge flow channels that are fluidly isolated from each water flow channel.

19. The dispenser of claim 18, wherein the dispenser controller controls dispensing of the water and each supplement composition from separate dispensers so as to deliver the supplement dosage formulation to the user.

20. The dispenser of claim 18, further comprising:
an input device configured to receive input from a user;
the dispenser controller being operably coupled with the input device, wherein the dispenser controller is configured to:
receive identification information input from a user via the input device;
obtain a supplement dosage formulation for the user based on a dietary supplement protocol of the user; and
control dispensing of water separately from each at least one supplement composition of the plurality of supplement cartridges to provide the supplement dosage formulation to the user.

21. A dietary supplement dispenser comprising:
a plurality of supplement cartridges, each supplement cartridge including a supplement composition that is different from the other supplement compositions of the other cartridges;
at least one dispenser fluidly coupled with the plurality of supplement cartridges;
an input device configured to receive input regarding a user;
a dispenser controller operably coupled with the plurality of supplement cartridges and input device, wherein the dispenser controller is configured to:
receive identification information input regarding the user via the input device;
obtain a supplement dosage formulation for the user based on a dietary supplement protocol of the user; and
control dispensing of at least one supplement composition of the plurality of supplement cartridges to provide the supplement dosage formulation to the user; and
a housing having a top region with a water bottle receiver and a bottom region with a water cooler receiver, thereby the housing being configured to fit between a water bottle and a water cooler.

22. A dietary supplement dispenser comprising:
a plurality of supplement cartridges, each supplement cartridge including a supplement composition that is different from the other supplement compositions of the other cartridges;
at least one dispenser fluidly coupled with the plurality of supplement cartridges;
an input device configured to receive input regarding a user;
a dispenser controller operably coupled with the plurality of supplement cartridges and input device, wherein the dispenser controller is configured to:
receive identification information input regarding the user via the input device;
obtain a supplement dosage formulation for the user based on a dietary supplement protocol of the user; and
control dispensing of at least one supplement composition of the plurality of supplement cartridges to provide the supplement dosage formulation to the user; and
a housing having a top region with a water bottle receiver, thereby the housing being configured to receive a gravity-fed water bottle.

23. A dietary supplement dispenser comprising:
a plurality of supplement cartridges, each supplement cartridge including a supplement composition that is different from the other supplement compositions of the other cartridges;
at least one dispenser fluidly coupled with the plurality of supplement cartridges;
an input device configured to receive input regarding a user;
a dispenser controller operably coupled with the plurality of supplement cartridges and input device, wherein the dispenser controller is configured to:
receive identification information input regarding the user via the input device;
obtain a supplement dosage formulation for the user based on a dietary supplement protocol of the user; and
control dispensing of at least one supplement composition of the plurality of supplement cartridges to provide the supplement dosage formulation to the user; and
the dispenser controller is operably coupled to at least one additive reservoir, wherein the dispenser controller is configured to determine at least one additive to be included in the supplement dosage formulation, and control dispensing of the at least one additive to provide the supplement dosage formulation to the user.

* * * * *